United States Patent
Hensley et al.

(10) Patent No.: US 12,383,754 B2
(45) Date of Patent: *Aug. 12, 2025

(54) MAGNETIC PARTICLE ACTUATION

(71) Applicant: Magnetic Insight, Inc., Alameda, CA (US)

(72) Inventors: Daniel Westbrook Hensley, Emeryville, CA (US); Matthias Weber, Oakland, CA (US); Elaine Yuiyi Yu, Alameda, CA (US); Robert Blayne Kettlewell, Berkeley, CA (US); Kyle David Fields, El Dorado Hills, CA (US); Patrick William Goodwill, Oakland, CA (US)

(73) Assignee: Magnetic Insight, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/394,573

(22) Filed: Dec. 22, 2023

(65) Prior Publication Data

US 2024/0157167 A1 May 16, 2024

Related U.S. Application Data

(63) Continuation of application No. 16/818,490, filed on Mar. 13, 2020, now Pat. No. 11,890,488.
(Continued)

(51) Int. Cl.
*A61N 2/12* (2006.01)
*A61B 5/00* (2006.01)
(Continued)

(52) U.S. Cl.
CPC .............. *A61N 2/12* (2013.01); *A61B 5/0036* (2018.08); *A61B 5/0071* (2013.01);
(Continued)

(58) Field of Classification Search
None
See application file for complete search history.

(56) References Cited

U.S. PATENT DOCUMENTS

| 4,538,130 A | 8/1985 | Gluckstern |
| 4,545,384 A | 10/1985 | Kawachi |

(Continued)

FOREIGN PATENT DOCUMENTS

| EP | 2223719 A1 | 9/2010 |
| EP | 2547253 | 1/2013 |

(Continued)

OTHER PUBLICATIONS

Goodwill, et al., "Projection X-Space Magnetic Particle Imaging," IEEE Transactions on Meidcal Imaging, Vo. 31, No. 5, May 2012, 10 pages.

(Continued)

*Primary Examiner* — Jason M Sims
*Assistant Examiner* — Matthew Eric Ogles
(74) *Attorney, Agent, or Firm* — Pillsbury Winthrop Shaw Pittman LLP

(57) ABSTRACT

Magnetic particle actuating systems may include a magnet system configured to generate a magnetic field that includes a field-free region. A corresponding control system can be configured to control the magnet system to create a field-free region at least partially matching a target region. An excitation system can be configured to generate an excitation field to cause actuation of magnetic nanoparticles in an actuation region.

19 Claims, 31 Drawing Sheets

Related U.S. Application Data

(60) Provisional application No. 62/818,052, filed on Mar. 13, 2019.

(51) Int. Cl.

| | | |
|---|---|---|
| *A61B 5/0515* | (2021.01) | |
| *A61B 5/055* | (2006.01) | |
| *A61B 6/03* | (2006.01) | |
| *A61B 8/00* | (2006.01) | |
| *G16H 20/40* | (2018.01) | |
| *G16H 30/20* | (2018.01) | |
| *G16H 40/63* | (2018.01) | |

(52) U.S. Cl.
 CPC ............ *A61B 5/0515* (2013.01); *A61B 5/055* (2013.01); *A61B 6/032* (2013.01); *A61B 8/00* (2013.01); *G16H 20/40* (2018.01); *G16H 30/20* (2018.01); *G16H 40/63* (2018.01)

(56) References Cited

U.S. PATENT DOCUMENTS

| | | | |
|---|---|---|---|
| 5,004,983 A | 4/1991 | Proksa | |
| 5,461,282 A | 10/1995 | Scheitrum | |
| 5,510,711 A | 4/1996 | Molyneaux | |
| 5,606,254 A | 2/1997 | Xie | |
| 5,965,214 A | 10/1999 | Crossfield | |
| 6,054,924 A | 4/2000 | Dames | |
| 6,076,007 A | 6/2000 | England | |
| 6,144,300 A | 11/2000 | Dames | |
| 6,204,766 B1 | 3/2001 | Crossfield | |
| 6,230,972 B1 | 5/2001 | Dames | |
| 6,323,769 B1 | 11/2001 | Dames | |
| 6,369,965 B1 | 4/2002 | Dames | |
| 6,486,655 B1 | 11/2002 | Crossfield | |
| 6,577,237 B1 | 6/2003 | Dames | |
| 6,595,419 B1 | 7/2003 | Doyle | |
| 7,300,452 B2 | 11/2007 | Gleich | |
| 7,351,194 B2 | 4/2008 | Gleich | |
| 7,758,622 B2 | 7/2010 | Gleich | |
| 7,778,681 B2 | 8/2010 | Gleich | |
| 8,757,166 B2 | 6/2014 | McKenna | |
| 8,847,592 B2 | 9/2014 | Goodwill | |
| 8,884,617 B2 | 11/2014 | Goodwill | |
| 8,968,171 B2 | 3/2015 | McKenna | |
| 9,274,084 B2 | 3/2016 | Goodwill | |
| 9,364,165 B2 | 6/2016 | Gleich | |
| 9,417,302 B2 | 8/2016 | Kuhn | |
| 9,451,900 B2 | 9/2016 | Boeve | |
| 9,682,247 B2 | 6/2017 | Susedik | |
| 9,687,668 B2 | 6/2017 | McKenna | |
| 9,763,594 B2 | 9/2017 | Goodwill | |
| 10,124,186 B2 | 11/2018 | McKenna | |
| 2003/0085703 A1 | 5/2003 | Gleich | |
| 2004/0075053 A1 | 4/2004 | Preikszas | |
| 2005/0073309 A1 | 4/2005 | Williams | |
| 2006/0211938 A1 | 9/2006 | Gleich | |
| 2006/0248944 A1 | 11/2006 | Gleich | |
| 2007/0258908 A1 | 11/2007 | Lanza | |
| 2008/0218162 A1 | 9/2008 | Ruhrig | |
| 2008/0309330 A1 | 12/2008 | Ohyu | |
| 2009/0115415 A1 | 5/2009 | Weaver | |
| 2010/0033171 A1 | 2/2010 | Gleich | |
| 2010/0052668 A1 | 3/2010 | Gleich | |
| 2010/0292564 A1 | 11/2010 | Cantillon Murphy | |
| 2011/0089942 A1 | 4/2011 | Goodwill | |
| 2011/0098558 A1 | 4/2011 | Weaver | |
| 2011/0221438 A1 | 9/2011 | Goodwill | |
| 2011/0306870 A1* | 12/2011 | Kuhn ................. | G01R 33/4808 600/12 |
| 2012/0058441 A1* | 3/2012 | Boeve ................. | G01R 33/1276 432/36 |
| 2012/0065491 A1 | 3/2012 | Borgert | |
| 2012/0100079 A1 | 4/2012 | Burdinski | |
| 2012/0265050 A1 | 10/2012 | Wang | |
| 2013/0241548 A1 | 9/2013 | Gleich | |
| 2014/0159712 A1 | 6/2014 | Graziani | |
| 2014/0206927 A1 | 7/2014 | Weinberg | |
| 2014/0306698 A1* | 10/2014 | Bontus .................. | G01R 33/02 324/234 |
| 2014/0320132 A1 | 10/2014 | Schmale | |
| 2015/0008910 A1 | 1/2015 | Goodwill | |
| 2015/0276902 A1 | 10/2015 | Weaver | |
| 2015/0285875 A1 | 10/2015 | Heidenreich | |
| 2015/0289939 A1 | 10/2015 | Rahmer | |
| 2015/0300987 A1 | 10/2015 | Rahmer | |
| 2015/0316628 A1 | 11/2015 | Heidenreich | |
| 2016/0317838 A1 | 11/2016 | Michaud | |
| 2016/0354495 A1 | 12/2016 | Harmer | |
| 2017/0128029 A1 | 5/2017 | Penfold | |
| 2017/0225003 A1 | 8/2017 | Gleich | |
| 2018/0017639 A1 | 1/2018 | Goodwill | |
| 2018/0017640 A1 | 1/2018 | Goodwill | |
| 2018/0017641 A1 | 1/2018 | Goodwill | |
| 2018/0335487 A1 | 11/2018 | Tonyushkin | |
| 2019/0079149 A1 | 3/2019 | Conolly | |
| 2020/0289839 A1 | 9/2020 | Hensley | |

FOREIGN PATENT DOCUMENTS

| | | |
|---|---|---|
| EP | 3143929 | 3/2017 |
| JP | 1209706 | 8/1989 |
| JP | 2011505952 | 3/2011 |
| JP | 2012525900 | 10/2012 |
| JP | 2013502262 | 1/2013 |
| JP | 2013123566 | 6/2013 |
| WO | 1996031790 | 10/1996 |
| WO | 1997048990 | 12/1997 |
| WO | 1998013708 | 4/1998 |
| WO | 1998015851 | 4/1998 |
| WO | 1999009436 | 2/1999 |
| WO | 1999048044 | 9/1999 |
| WO | 2000010123 | 2/2000 |
| WO | 2004091395 | 10/2004 |
| WO | 2008099331 | 8/2008 |
| WO | 2010008478 | 1/2010 |
| WO | 2011010243 | 1/2011 |
| WO | 2011116229 | 9/2011 |
| WO | 2018013738 | 1/2018 |

OTHER PUBLICATIONS

Bringout, et al. "Coil Design for Magnetic Particle Imaging: Application for Preclinical Scanner," IEEE Transactions on Magnetics, vol. 51, No. 2, Feb. 2015. 8 pages.
International Society for Magnetic Resonance in Medicine, ISMRM, No. 406, May 15, 2015, XP040666089. 1 page.
U.S. Appl. No. 15/674,234, filed Aug. 10, 2017, Goodwill Patrick W.
PCT App. No. PCT/US2017/041783; International Search Report and Written Opinion mailed Nov. 21, 2017; 14 pages.
Gleich et al., Tomographic imaging using the nonlinear response of magnetic particles, Nature, 435(7046): 1214-7, Jun. 2005.
PCT App. No. PCT/US2011/028879; International Search Report and Written Opinion mailed Oct. 19, 2011. 7 pages.
PCT App. No. PCT/US2011/028879; Preliminary Report on Patentability Chapter I mailed Sep. 18, 2012. 5 pages.
EP App. No. 16173404.1; European Search Report and Written Opinion mailed Jan. 25, 2017. 7 pages.
Biederer, S et al.; "A Spectrometer for Magnetic Particle Imaging," IFMBE Proceedings (International Federation for Medical and Biological Engineering), Springer, DE, vol. 22, No. 3, Feb. 4, 2009, pp. 2313-2316, XP009130408, ISSN: 1680-0737, DOI: 10.1007/978-3-540-89208-3_555.
Goodwill and Conolly; Multidimensional x-space Magnetic Particle imaging, IEEE Transactions on Medical Imaging, 30(9): (2011) 1581-1590, ISSN 1558-254X.
PCT App. No. PCT/US2017/041792; International Search Report and Written Opinion mailed Oct. 16, 2017; 10 pages.

(56) References Cited

OTHER PUBLICATIONS

Konkle, J J et al.; "Twenty-fold acceleration of 3D projection reconstruction MPI", Biomedizinische Technik Walter De Gruyter Germany, vol. 58. No. 6. , Dec. 2013 (Dec. 2013), pp. 565-576, XP002773942, ISSN: 0013-5585.
Weber, Matthias et al.; "MPI with a mechanically rotated FFL", 2015 5th International Workshop on Magnetic Particle Imaging (IWMPI), IEEE, Mar. 26, 2015 (Mar. 26, 2015), p. 1, XP032776021, DOI: 10.1109/IWMPI.2015.7107026, ISBN: 978-1-4799-7269-2.
PCT App. No. PCT/US2009/003764; International Search Report and Written Opinion mailed Jan. 15, 2010. 7 pages.
PCT App. No, PCT/US2009/003764; Preliminary Report on Patentability Chapter I mailed Jan. 5, 2011. 5 pages.
Goodwill, Narrowband and x-Space Magnetic Particle Imaging, dissertation, 2010, 91 pages.
Knopp et al., Trajectory analysis for magnetic particle imaging, Dec. 2008, p. 386.
Kovács, Attila, "Scanning strategies for imaging arrays," Proc. SPIE 7020, Millimeter and Submillimeter Detectors and Instrumentation for Astronomy IV, 702007 (Jul. 18, 2008); doi: 10.1117/12.790272. 17 pages.
Crossfield, Mike., "Have null, will fly," Mike Crossfield describes a novel approach to low-cost data tagging. IEE Review. (Jan. 2001), pp. 31-34.
Karsten, Robert P., "The Use of Flying Null Technology in the Tracking of Labware in Laboratory Automation." Downloaded from jla.sagepub.com, at Univ California Berkeley Lib, Jun. 16, 2015. 4 pages.
Sparavigna, Amelia. "Labels discover physics: the development of new labelling methods as a promising research field for applied physics." Dipartimento di Fisica, Politecnico di Torino. Corso Duca degli Abruzzi 24, Torino, Italy, pp. 1-16.
PCT App. No. PCT/US2017/041792; Preliminary Report on Patentability Chapter 1 mailed Jan. 15, 2019.
International Search Report and Written Opinion, PCT Appl. No. PCT/US2020/0226988, mailed May 29, 2020, 12 pages.

* cited by examiner

MAGNETIC PARTICLE ACTUATION

CROSS-REFERENCE TO RELATED APPLICATIONS

The current application is a continuation of and claims priority to U.S. patent application Ser. No. 16/818,490 filed Mar. 13, 2020 and entitled "MAGNETIC PARTICLE ACTUATION," which claims priority to U.S. Provisional Patent Application No. 62/818,052 filed Mar. 13, 2019 and entitled "MAGNETIC PARTICLE ACTUATION," the contents of which are hereby incorporated by reference in their entirety.

BACKGROUND

Magnetic nanoparticles (MNPs) can be utilized in the diagnosis and treatment of certain medical conditions. Exemplary treatments can include tissue ablation, drug/payload delivery (e.g., carried by MNPs), hyperthermia (the heating of tissue, typically to kill cancerous tissues), the use of MNPs as a potentiator or adjuvant for other therapies such as chemo and/or radiation therapy, etc. These treatments can be performed in part by "actuating" the MNPs causing local heating, breaking apart of aggregate structures (as with drug/payload delivery), etc. Actuation may be performed by applying an RF field to the MNPs within the patient.

SUMMARY

Systems, methods, and computer program products are disclosed that may allow the generating a of magnetic field with a magnet system, where the magnetic field includes a field-free region at least partially matching a target region. Also, an excitation field may be applied with an excitation system to cause actuation of magnetic nanoparticles in an actuation region. In some embodiments, at least partially matching the field-free region to the target region can include enclosing the target region within the field-free region, conforming the field-free region to the target region, or avoiding overlap with a region to avoid. Additional target region(s) may be determined during a process of covering an entire therapeutic region to be actuated during a treatment, while avoiding actuation of a region to avoid.

Also, the at least partial matching of the field-free region to the target region can be performed by translating the field-free region to the target region, scaling the field-free region, changing a shape of the field-free region, or rotating-the field free region. Further, the at least partial matching of the field-free region to the target region can include causing mechanical movement of one or more magnets or magnetic materials in the magnet system to translate, scale, rotate, or change the shape of the field-free region. The magnet system can also include one or more electromagnets and the at least partial matching of field-free region to the target region can be based at least on controlling current(s) in the one or more electromagnets.

An excitation system can apply the excitation field, for example, by generating the excitation field in a manner that changes the actuation region. Generating of the excitation field can be performed through multiple independently controllable RF coils to enable changing the actuation region along multiple axes. Also, the multiple independently controllable RF coils can allow selection of an RF vector along which the actuation region can be changed through specifying currents through the multiple independently controllable RF coils. The generating of the excitation field can also be performed through at least one spatially inhomogeneous RF coil.

In some embodiments, an image of the patient can be obtained and the field-free region can be located and/or shaped to approximately coincide with the target region identified based at least on the image. In other embodiments, a treatment plan for the target region can be received, with the treatment plan specifying the actuation to be delivered to the magnetic nanoparticles. One or more images of the patient can be generated or received, and the actuation can be automatically modified based at least on a change in the patient, a change in the magnetic nanoparticles, or a change in a predicted dose as determined from the one or more images. The excitation field can be applied to perform the modified actuation. Also, a magnetic particle imaging signal can be received simultaneously with application of the excitation field. An actuation dose can be determined based at least on a calculation using the magnetic particle imaging signal and the excitation field can be modified based at least on the actuation dose.

In some embodiments, a magnetic particle imaging system can include a magnet system configured to generate a magnetic field that includes a field-free region, an excitation system configured to generate an excitation field to cause actuation of magnetic nanoparticles in an actuation region, a control system configured to control the magnet system to create a field-free region at least partially matching a target region. The magnetic particle actuating system can also include an RF shield disposed between a portion of the excitation system and a portion of the magnet system to reduce interference of the excitation system during the generation of the excitation field.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

The application of an RF field to magnetic nanoparticles (MNPs) can be used to induce changes in a subject or treat patient conditions, for example, macroscopically heating a treatment site in a patient, breaking apart/physically changing MNPs or MNP aggregate constructs to deliver a drug to a treatment site, or stimulating differential gene activation through microscopic or macroscopic heat generation. Using MNPs to generate heat in tissues can be an effective treatment for some cancers. Specifically, MNPs located at a tumor can be heated in a controlled manner to cause or assist with the killing of cancerous tissue.

It is believed that the heat generated by excitation of MNPs is caused by the combined effect of hysteresis (resistive heating from induction caused by reorienting the MNPs magnetic dipole), the Neel effect (heating due to induced currents resulting from supermagnetism), and frictional heating (changing the physical alignment of MNPs, where the energy delivered to the moving MNPs cause a frictional heating of the nearby tissue).

Figure 1A:
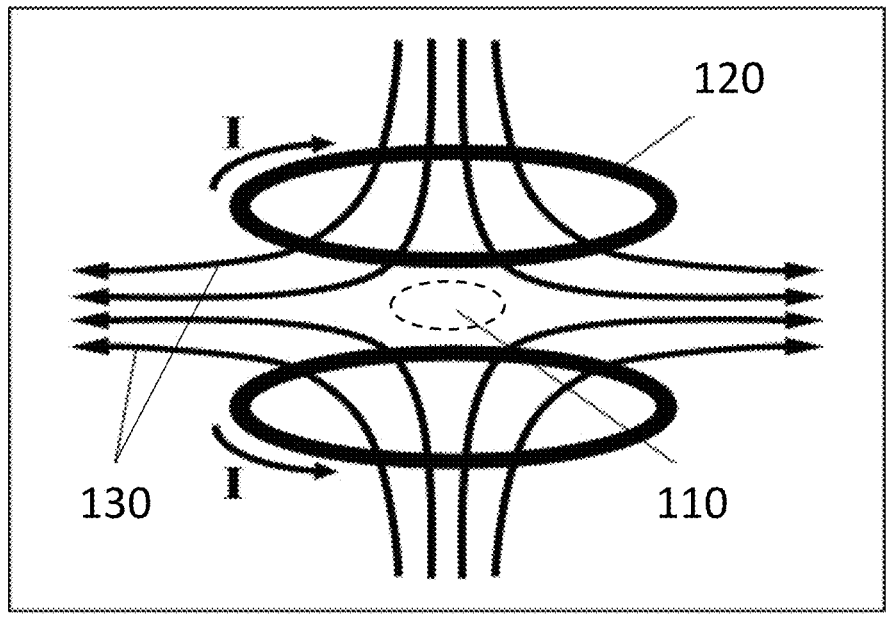
FIG. 1A is a diagram illustrating a simplified perspective of an exemplary coil system and FFR in accordance with certain aspects of the present disclosure.
Figure 1B:
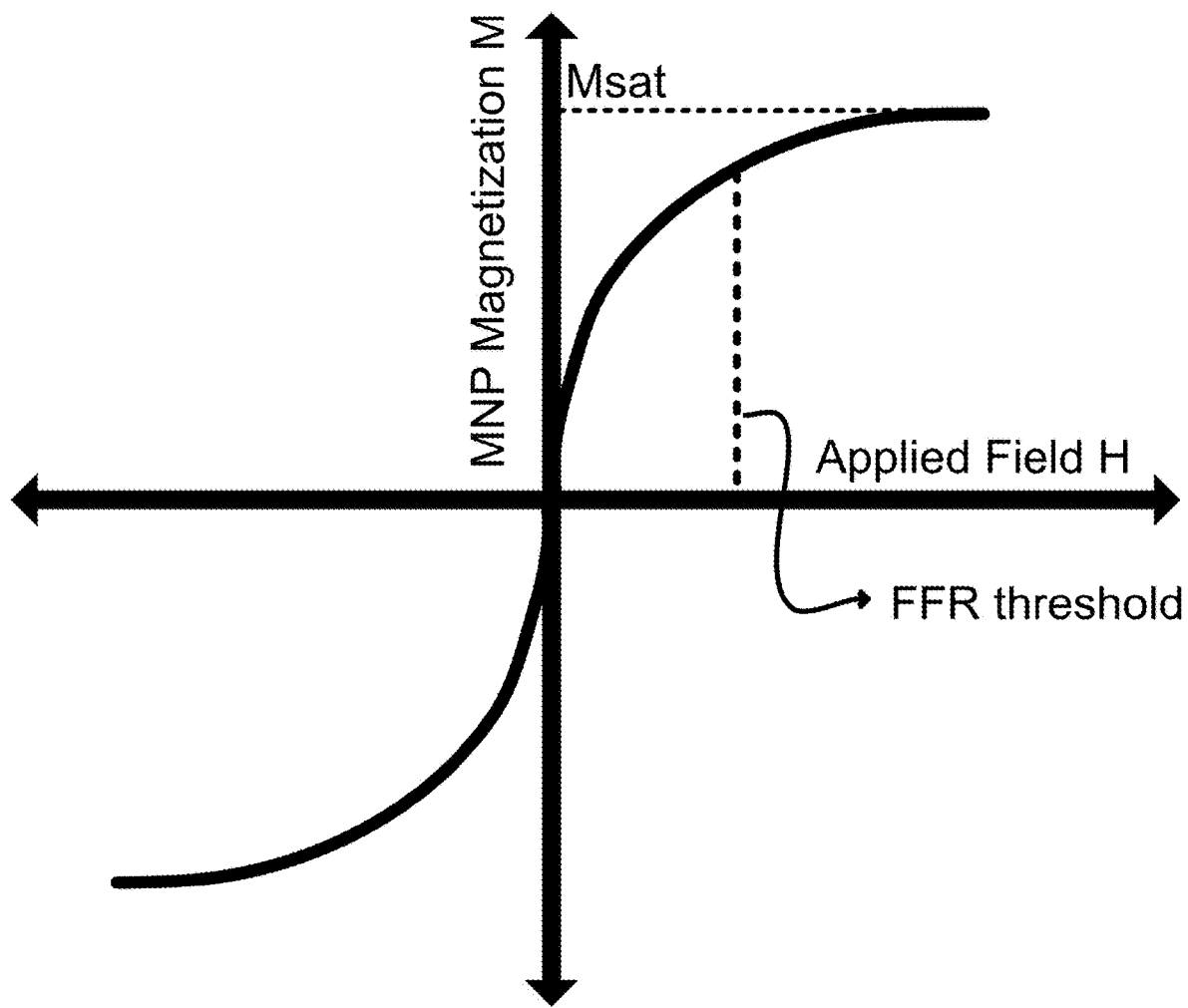
FIG. 1B is a diagram illustrating an exemplary magnetization curve illustrating a threshold for defining a FFR in accordance with certain aspects of the present disclosure.

The present disclosure expands on the general actuation art, in part, through the utilization of magnetic Field Free Region concepts, which can assist in the localization of where MNP actuation will take place. Spatial localization can be affected by the nonlinear magnetic saturation phenomena of MNPs. The magnetization or M-H curve of many MNPs is "S-shaped" as shown in FIG. 1B because they exhibit saturation. Higher applied field strengths thus achieve less and less increase in the magnetization of an MNP, eventually plateauing, such that further increases in field magnitude yield no detectable change in magnetization magnitude. Therefore, with the application of a strong spatial gradient field, MNPs within some small region can be unsaturated (this region may be referred to herein as the "field-free region" or FFR). MNPs outside of this FFR are essentially locked in place and therefore an alternating-current (AC) RF field can preferentially actuate (e.g., lead to heat generation) particles in the vicinity of the FFR. For actuation applications that do not necessarily involve macroscopic heat generation, e.g., drug delivery or gene activation, this spatial localization concept remains true, although the physical details will differ.

In the most general sense, an FFR is a region of lower magnetic field magnitude distinguished from a surrounding or adjacent region of higher magnetic field magnitude. An FFR can be established at a certain location through the creation of a magnetic null. One example of the creation of a FFR 110 is shown in FIG. 1A, which illustrates two coils 120 where currents with equal magnitude but flowing in opposite directions in the coils generate opposing magnetic fields 130. An FFR is formed surrounding the region between the coils where the magnetic field transitions through zero field strength.

The overall shape and structure of an FFR is determined by the orientation and strength of magnets and magnetic materials generating a magnetic field with a nonzero spatial gradient at least somewhere in a volume of interest. Complex or asymmetric orientations of magnets and magnetic materials can generate complex or asymmetric FFRs as illustrated in the example shown in FIG. 22. The magnetic characteristics of an MNP of interest, e.g., to be actuated, can be used to further determine specific sizing and contours of an FFR. For example, in the field of magnetic particle imaging, a magnetic field gradient and MNP M-H curve can define a point-spread function (PSF) that defines how well an FFR spatially localizes signals from an MNP. Various metrics such as the full-width-at-half-maximum (FWHM) of the PSF or contours created by applying thresholds to the magnitude of the magnetic field in a volume can be used to identify the FFR shape (e.g., the FFR is the region of space where the magnetic field magnitude is less than some value). For example, as illustrated in FIG. 1B, in some embodiments, the threshold for the FFR can be an applied field strength, or some fraction thereof, associated with inflection in the M-H curve for a MNP due to magnetic saturation. Depending on the M-H curve of an MNP, an inflection point may be identified in the range of 1-100 mT, for example. In other embodiments, a threshold may be determined by the applied field strength at which the MNP achieves substantial magnetization saturation (e.g., 95% or 99% of Msat, the maximum magnetic saturation for an MNP, as illustrated in FIG. 1B). In other embodiments, the threshold may be the field amplitude where 80%, 70%, 60%, 50%, 40%, 30%, 20%, or 10% Msat is achieved, or essentially no magnetic field. In other embodiments, the threshold may be chosen as some absolute field value that pertains to an actuation physics.

While the term field "free" region is a bit of a misnomer (and while an absolute delineation of an FFR can be elusive, as seen from the discussion above), for the purpose of the present disclosure, an FFR is generally a region of low magnetic field adjacent to or surrounded by a region of higher magnetic field. Furthermore, regardless of how field thresholds to identify contours of interest are chosen, the shape of an FFR is determined by the spatial structure of the total applied magnetic field, which is fully determined by arrangements and strengths of magnets and magnetic materials.

As used herein, embodiments of a field-free region (FFR) may be optionally described as a field-free point (FFP) or a field free line (FFL). A field free point or FFP refers to an approximately elliptical region of low magnetic field. A field-free line or FFL is generally an FFR elongated greatly along one axis, having a length and a thickness, where the magnetic field is similarly low. As used herein, a "field-free region" is understood to account for the reality that it may not be a perfectly straight line, a perfect ellipsoid, nor completely absent a magnetic field, but that such are often goals in the creation of an FFR. Also, as discussed further herein, the FFR need not have a regular geometric shape and can instead be shaped or formed to have an irregular shape or other shape as called for by a particular application and as generated by a particular system/magnet configuration. As discussed below, flexibility in the shaping of an FFR can provide technical benefits for the purposes of actuating MNPs in a patient.

As used herein, a "patient" can mean any living or nonliving object that may contain the magnetic nanoparticles. A patient can be, for example, a human, or an animal subject. In other cases, an inanimate object that may contain magnetic nanoparticles for calibration or research purposes may be referred to as a patient.

In most applications of the present disclosure, it can be a goal to deposit energy into a target region (e.g., a tumor) where there may be an accumulation of magnetic nanoparticles. Often this will be for the purpose of applying a therapy to a patient. Accordingly, as used herein, a "target region" is generally a region intended for treatment. There may be an accumulation of magnetic particles in regions that are not intended to be actuated (e.g., MNPs that have accumulated in a patient's healthy liver). As used herein, such regions are referred to as "region(s) to avoid." Furthermore, different target regions may be distinguished from each other at least to apply different degrees or extents of actuation.

In one embodiment, target regions can be identified in MPI images taken of the subject, or alternatively using an imaging modality that can be co-registered with the magnet particle actuator system (e.g., through the use of common fiducial markers). Target regions for actuation may be identified manually by a user or automatically using an algorithm. A computerized program can then calculate and execute optimal actuation procedures.

In some embodiments, the procedure can include a discrete number of actuation steps to actuate target regions. In other embodiments, continuously varying FFR trajectories are prescribed, or some combination of both.

In certain embodiments of the present disclosure, it can be a goal to match an FFR with a target region. As described further below, FFRs may be translated, scaled, and reshaped using aspects of a magnet system. For example, an FFR shape may be linearly and isotropically scaled in all dimensions by increasing or decreasing the distance between certain magnets. The same can be accomplished by symmetric radial expansion or shrinking of magnet arrangements. In some cases, simple scaling of an FFR will accomplish the desired matching of the FFR to a target region. In other cases, reshaping of the FFR will be required. As will be discussed, myriad FFR shapes can be created by independently translating magnetic materials and/or changing currents in electromagnets included within the magnet system.

As described in further detail below, the present disclosure provides systems, methods and computer software that enable modification of an FFR in order to better approximate a desired actuation region. To provide for actuation of MNPs, embodiments of the present disclosure can include generating a magnetic field with a magnet system, the magnetic field including a field-free region at least partially matching a target region. To then actuate the MNPs, an excitation field can be applied with an excitation system to cause actuation of magnetic nanoparticles in an actuation region.

Figure 2:
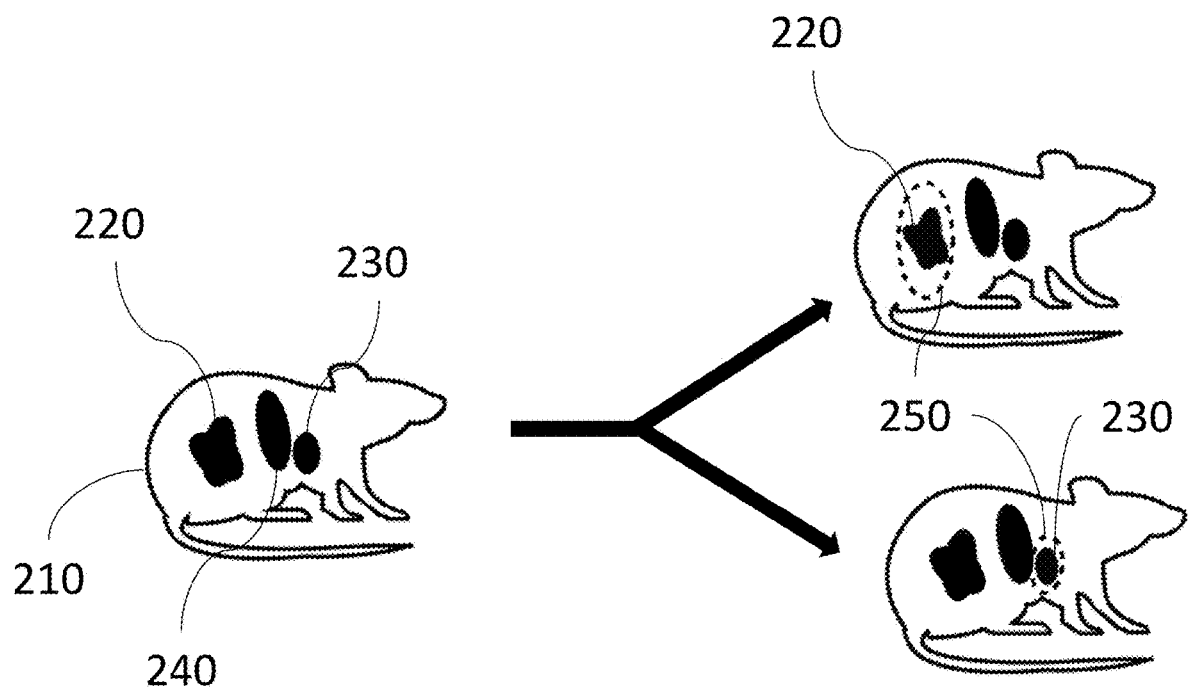
FIG. 2 is a diagram illustrating an exemplary at least partial matching of a FFR to target regions in a patient in accordance with certain aspects of the present disclosure.

One example of at least partial matching of FFRs to target regions is illustrated in FIG. 2. Here, a patient 210 (in this case, a rat) is illustrated on the left as having target regions 220, 230 and region to avoid 240. On the upper right, FFR 250 is illustrated as enclosing target region 220. This allows a localized actuation of MNPs in target region 220. Then, as shown on the lower right, FFR 250 can be moved and modified to enclose the other target region 230. In this way, one or more target regions can be selected for actuation and treatment by placement and shaping of an FFR, while not actuating a region to avoid.

When "at least partially matching a target region" with an FFR, it is contemplated that the intended degree of matching may take into account 1) the fact that excitation fields will rapidly alter the location and possibly shape of the FFR in an oscillatory fashion. As discussed herein, an actuation region can be the total volume the shaped FFR impinges during excitation, and 2) the fact that having the actuation region match the target region is a primary consideration in actuation. Thus, an FFR may be created that does not entirely match a target region statically, but when combined with the effects of the excitation field the actuation region will nonetheless more accurately match the target region.

Figure 3:
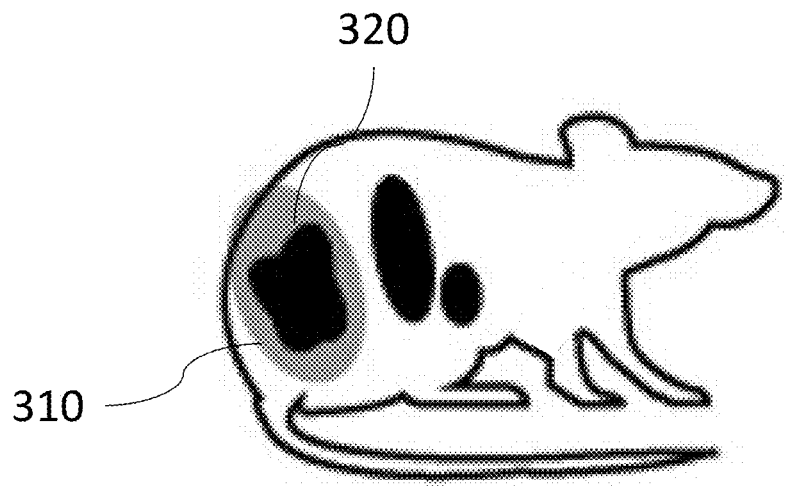
FIG. 3 is a diagram illustrating an exemplary enclosing of a target region with a FFR in accordance with certain aspects of the present disclosure.

The present disclosure contemplates numerous ways in which the FFR may be at least partially matched to the target region. In some implementations, at least partially matching the field-free region to the target region can include enclosing the target region within the field-free region. One example of enclosing a target region is illustrated in FIG. 3, showing FFR 310 enclosing target region 320 such that MNPs in the entire target region can potentially be actuated for treatment.

Figure 4:
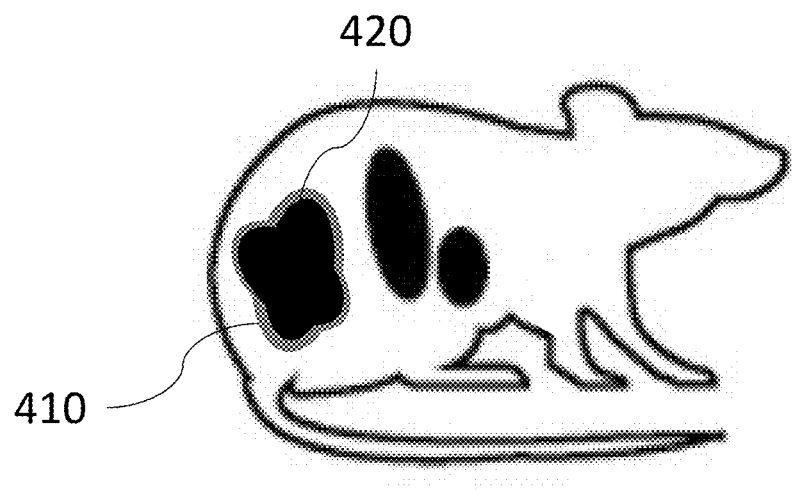
FIG. 4 is a diagram illustrating an exemplary conforming of a FFR with a target region in accordance with certain aspects of the present disclosure.

In some implementations, at least partially matching the field-free region to the target region can include conforming the field-free region to the target region. One example of conforming an FFR to a target region is illustrated in FIG. 4, showing an FFR 410 that has been shaped to conform closely with target region 420, allowing a highly efficient actuation of MNPs at the target region. "Conforming," as used herein, can mean replicating the shape of the target region, but more typically is intended to mean approximating the target region with some excess margin (as shown in FIG. 4). For example, in various embodiments, the FFR may exceed the target region by 5%, 10%, 20%, etc. or, alternatively, by 2 mm, 3 mm, 4 mm, etc.

Figure 5:
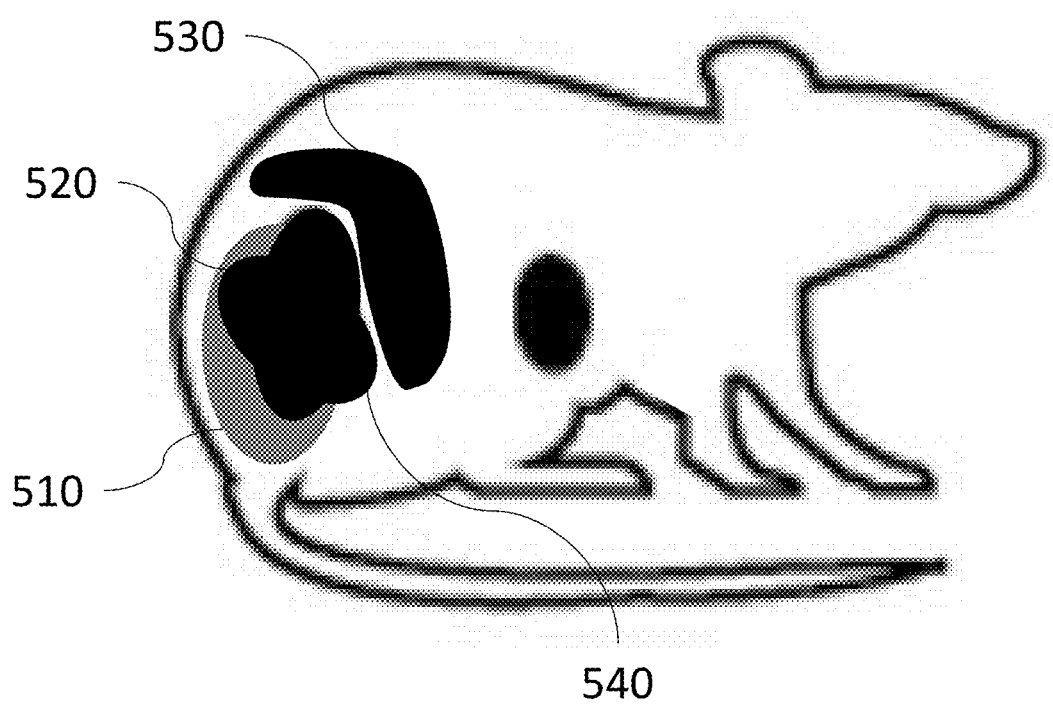
FIG. 5 is a diagram illustrating an exemplary of a FFR not overlapping with a region to avoid in accordance with certain aspects of the present disclosure.

Due to limitations of the system or the anatomy and treatment needs of the patient, it may not always be possible to provide full coverage of a target region by the FFR. Therefore, in some implementations, at least partially matching the field-free region to the target region can include avoiding overlap with a region to avoid. One example of enclosing a target region is illustrated in FIG. 5, showing FFR 510 enclosing a portion of the target region 520, while the remaining portion 540 of the target region is unable to be enclosed by this FFR due to the shape of nearby region to avoid 530. The present disclosure contemplates that the enclosing, conforming, and avoiding of overlap with a region to avoid can be achieved in part by utilizing changes in the FFR caused by the excitation field.

Figure 6:
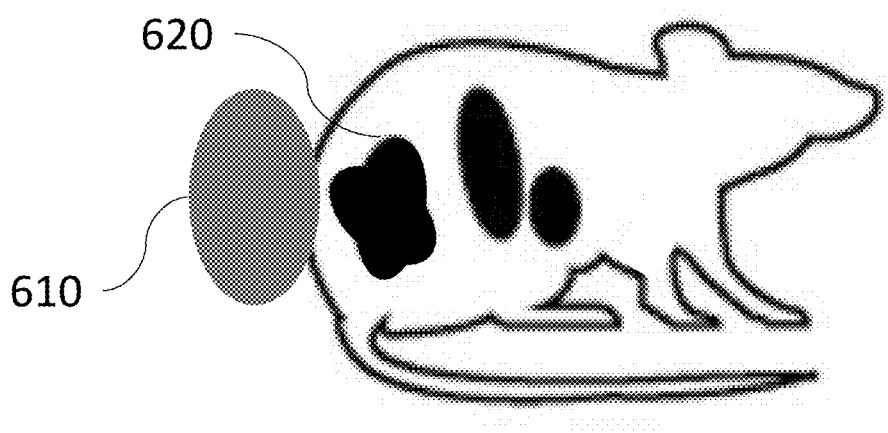
FIG. 6 is a diagram illustrating an exemplary translating of a FFR in accordance with certain aspects of the present disclosure.
Figure 6:
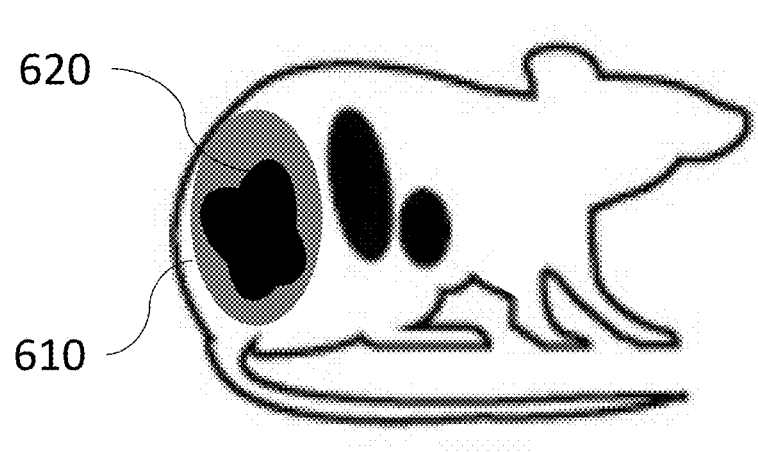

The types of matching described above can be implemented according to any combination of operations for generating, shaping, moving, etc., of the FFR. For example, in some implementations, at least partially matching the field-free region to the target region can include translating the field-free region to the target region. One example of translating the FFR is illustrated in FIG. 6. The top portion of FIG. 6 illustrates a patient where FFR 610 is not in position to cover target area 620. In the bottom portion of FIG. 6, the FFR has been translated such that it covers the target area.

Figure 7:
FIG. 7 is a diagram illustrating an exemplary scaling of a FFR in accordance with certain aspects of the present disclosure.
Figure 7:
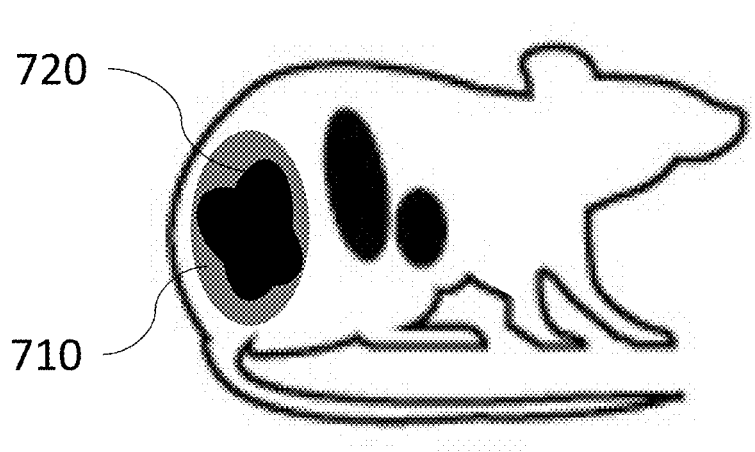

In some implementations, at least partially matching the field-free region to the target region can include scaling the field-free region. One example of scaling the FFR is illustrated in FIG. 7. The top portion of FIG. 7 illustrates a patient where FFR 710 is too small to cover the target area 720. In the bottom portion of FIG. 7, FFR 710 has been scaled to enlarge the FFR such that it covers target area 720.

Figure 8:
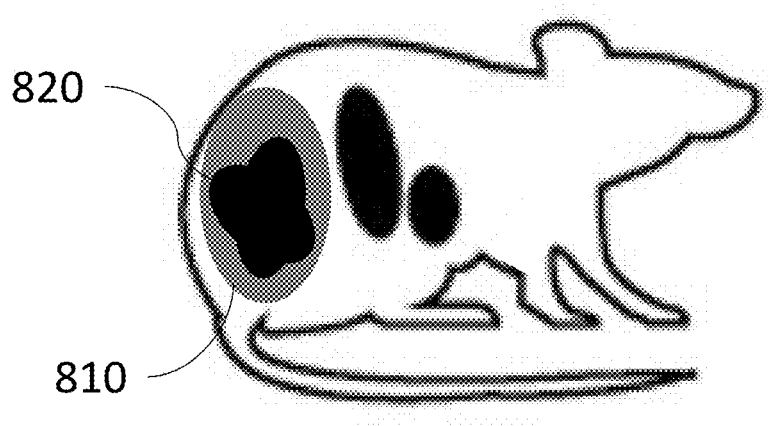
FIG. 8 is a diagram illustrating an exemplary shaping of a FFR in accordance with certain aspects of the present disclosure.
Figure 8:

In some implementations, at least partially matching the field-free region to the target region can include changing the shape of the field-free region. One example of changing a shape of the FFR is illustrated in FIG. 8. The top portion of FIG. 8 illustrates a patient where FFR 810 covers target area 820 but could result in actuation of MNPs that are outside the target area. In the bottom portion of FIG. 8, FFR 810 has been changed in shape to improve the matching of the FFR to target region 820.

Figure 9:
FIG. 9 is a diagram illustrating an exemplary rotating of a FFR in accordance with certain aspects of the present disclosure.
Figure 9:
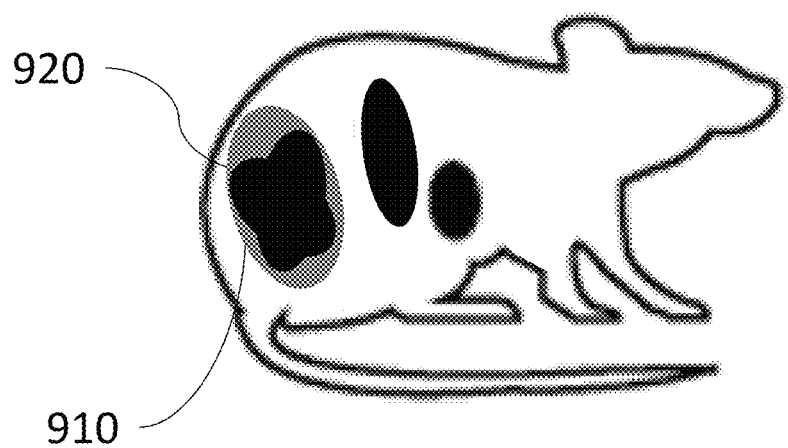

In some implementations, at least partially matching the field-free region to the target region can include rotating the field-free region. One example of rotating the FFR is illustrated in FIG. 9. The top portion of FIG. 9 illustrates a patient where FFR 910 is generally shaped to target region 920, however it is still unable to efficiently cover the target region. In the bottom portion of FIG. 9, FFR 910 has been rotated such that the matching of the target area 920 is improved.

An actuation region is a region where MNPs are actuated. As used herein, an "actuation region" is typically of the same extent or larger than the target region. In some embodiments, the actuation region can be the region impinged by the shaped FFR during actuation. This can be influenced by a statically (i.e., not considering RF excitation effects) matched FFR shape and location and also by the path an RF excitation field translates the FFR through during actuation (along with any further shaping—as would happen with an inhomogeneous RF field).

Implementations of the current subject matter can include determining additional target region(s) during a process of covering an entire therapeutic region to be actuated during a treatment, while avoiding actuation of a region to avoid. In some treatments, it may be necessary or desirable to treat an entire therapeutic region in a manner that requires determining multiple target regions.

Figure 10:
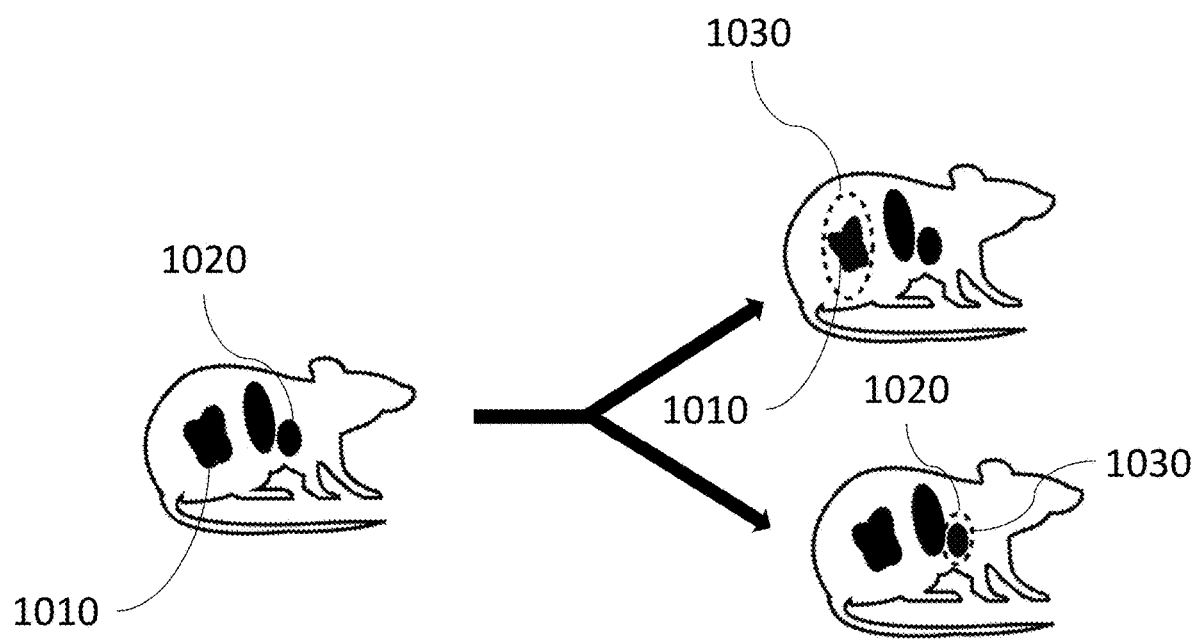
FIG. 10 is a diagram illustrating an exemplary actuation of additional target regions in accordance with certain aspects of the present disclosure.

In one simple example, as illustrated in FIG. 10, a patient can have multiple target regions 1010, 1020. Target regions can be distinguished by physical separation and/or different actuation extents or protocols. The additional target regions can then be actuated in series as shown in the right portion of FIG. 10 where one target region 1010 is actuated based on location of FFR 1030 and then the other target region 1020 can be actuated after FFR 1030 has been moved and reshaped.

Figure 11:
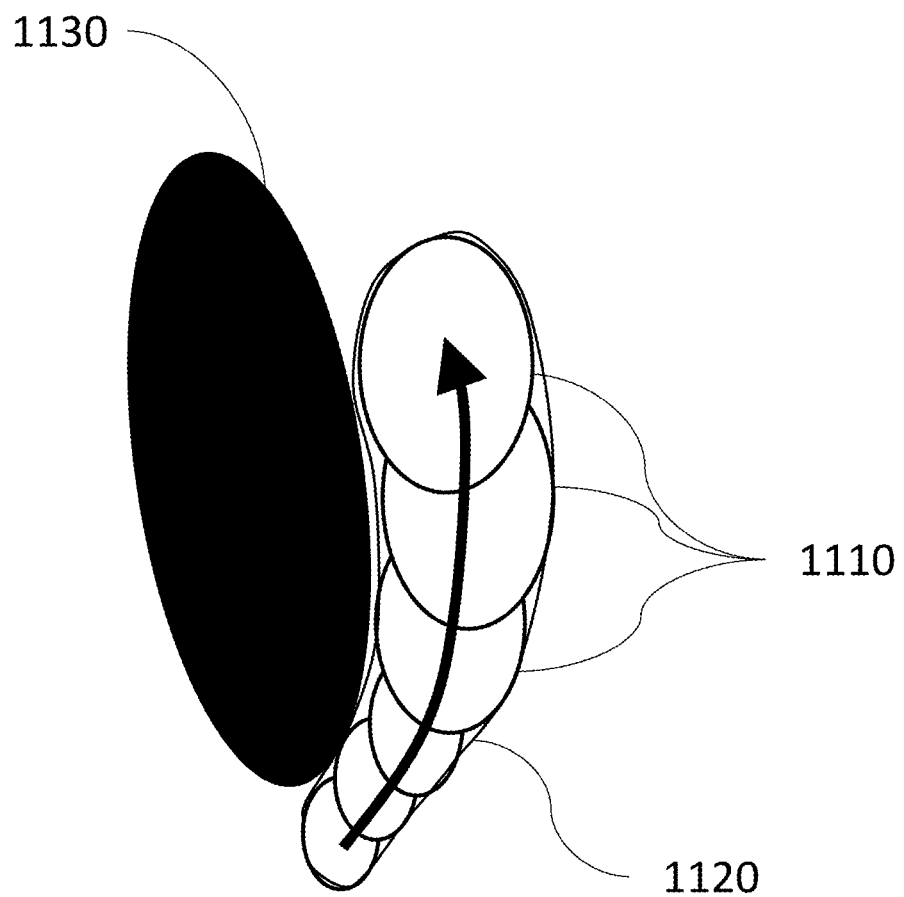
FIG. 11 is a diagram illustrating an exemplary continuous activation of target regions in a patient in accordance with certain aspects of the present disclosure.

In some cases, continuous movement of an FFR may be used in conjunction with FFR shaping to achieve more complex desired actuation procedures. One example of continuously moving an FFR to allow actuation of a complex target shape is illustrated in FIG. 11. The continuous movement of FFR 1110 is illustrated by the snapshots of the FFR position and shape at a number of times. The continuous manner of actuating would then result in the envelope 1120 shown, which would correspond to an actuation region having the complex shape shown and avoiding actuation in a region to avoid 1130. Accordingly, some implementations of the current subject matter can allow for actuation of regions having complex shapes by performing actuating of additional target regions in a continuous manner.

By moving an FFR through a defined volume, actuation regions can be formed with more complex shapes and potentially larger total volumes of actuation than that which can be accomplished with a shaped, but fixed mean FFR location. Since the FFR shape can be modified while moving the FFR, this makes it possible to draw more precise treatment contours (e.g., to conform the actuation region to a tumor shape, or when nearing regions to avoid).

Furthermore, depending on the type and degree of actuation application, the combination of FFR shaping and dynamic movement can be leveraged to navigate an optimal tradeoff space between continual actuation/residence time and overall actuation coverage. For example, in some cases it will be more desirable to constantly and completely actuate a subregion of a target region for a period of time, then move to another subregion, and so forth. In other cases, it may more desirable to scan from subregion to subregion and back and forth whereby actuation of all subregions is completed after some number of such cycles.

Continuous movement of an FFR, as described above, is distinguished from dynamic RF excitation trajectories (discussed further below) at least by having lower temporal bandwidth and potentially higher power. As such, this dynamic movement of the FFR may contribute little or nothing to actuation directly, only by moving the RF-oscillating FFR through target volumes. In this manner, the FFR can be moved more slowly across a larger volume than that possible by changing RF excitation parameters dynamically. In some embodiments, dynamic FFR movement can be provided by electromagnets in the magnet system with a temporal bandwidth less than or equal to 1 kHz.

Figure 12:
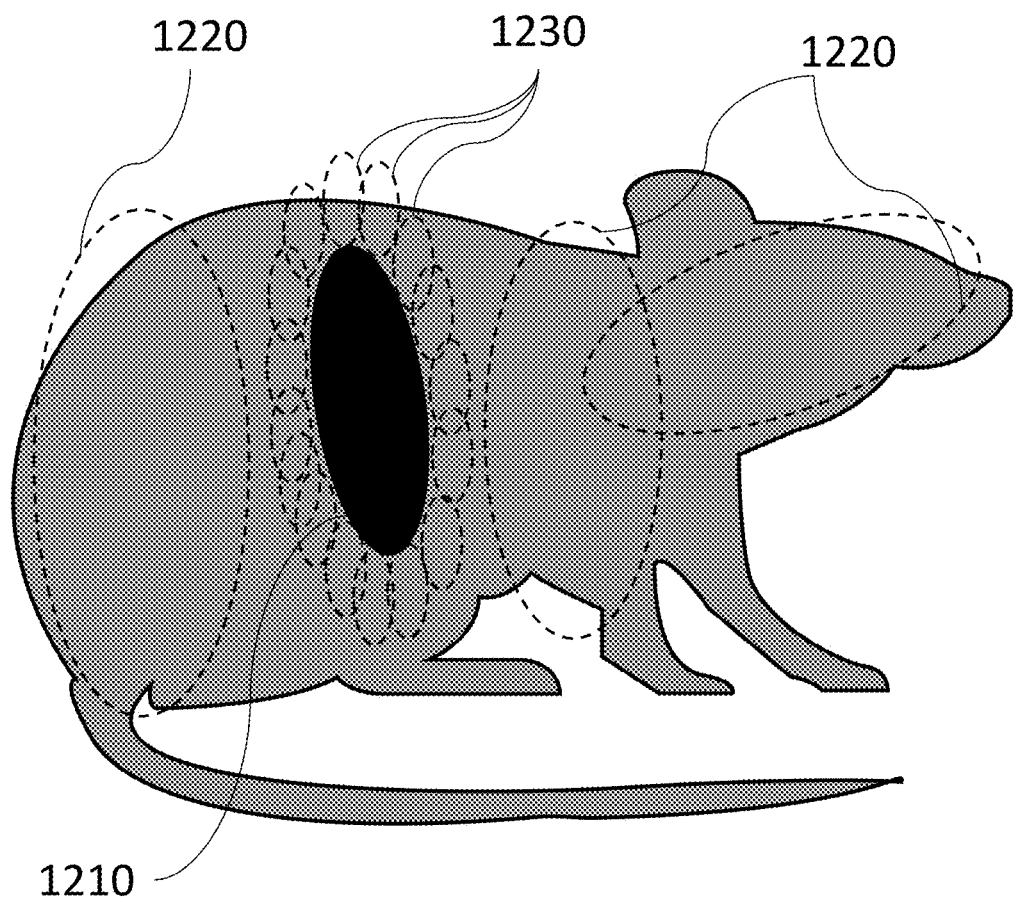
FIG. 12 is a diagram illustrating an exemplary actuation of an entire patient except for a region to avoid in accordance with certain aspects of the present disclosure.

Other implementations can include having the entire therapeutic region to be actuated as essentially the entire patient, other than a region to avoid. A simplified example of such is depicted in FIG. 12. Here, the patient has a region to avoid 1210, shown by the dark region in the center of the patient. Systems disclosed herein can apply multiple or continuous actuations to cover the entire patient (depicted here by shading throughout the patient). In one implementation, large FFRs 1220 can be used for large actuation regions that may cover large sections (or the majority) of the patient while the region(s) to avoid can avoid being actuated by using smaller FFRs 1230 (illustrated in FIG. 12 by dashed outlines proximate the region to avoid).

When the term "essentially the entire patient" is used herein, it is contemplated that such could refer to just a significant portion of a patient—for example, essentially the entire patient located within the scanner (in the case where the scanner may not fit the whole body of the patient). Similarly, it may refer to a macroscopic section of a patient, for example, actuation of a fraction (e.g., half, quarter, etc.) of the patient (e.g., upper abdomen or lower abdomen).

It should also be noted that when the present disclosure describes "avoiding" a region, such does not require that there be absolutely zero actuation in such a region but rather that an effort is made to substantially limit actuation in the region to avoid. As is understood, field-free regions and actuation regions do not necessarily have sharp boundaries and therefore a small amount of actuation may occur in a region trying to be avoided.

Figure 13:
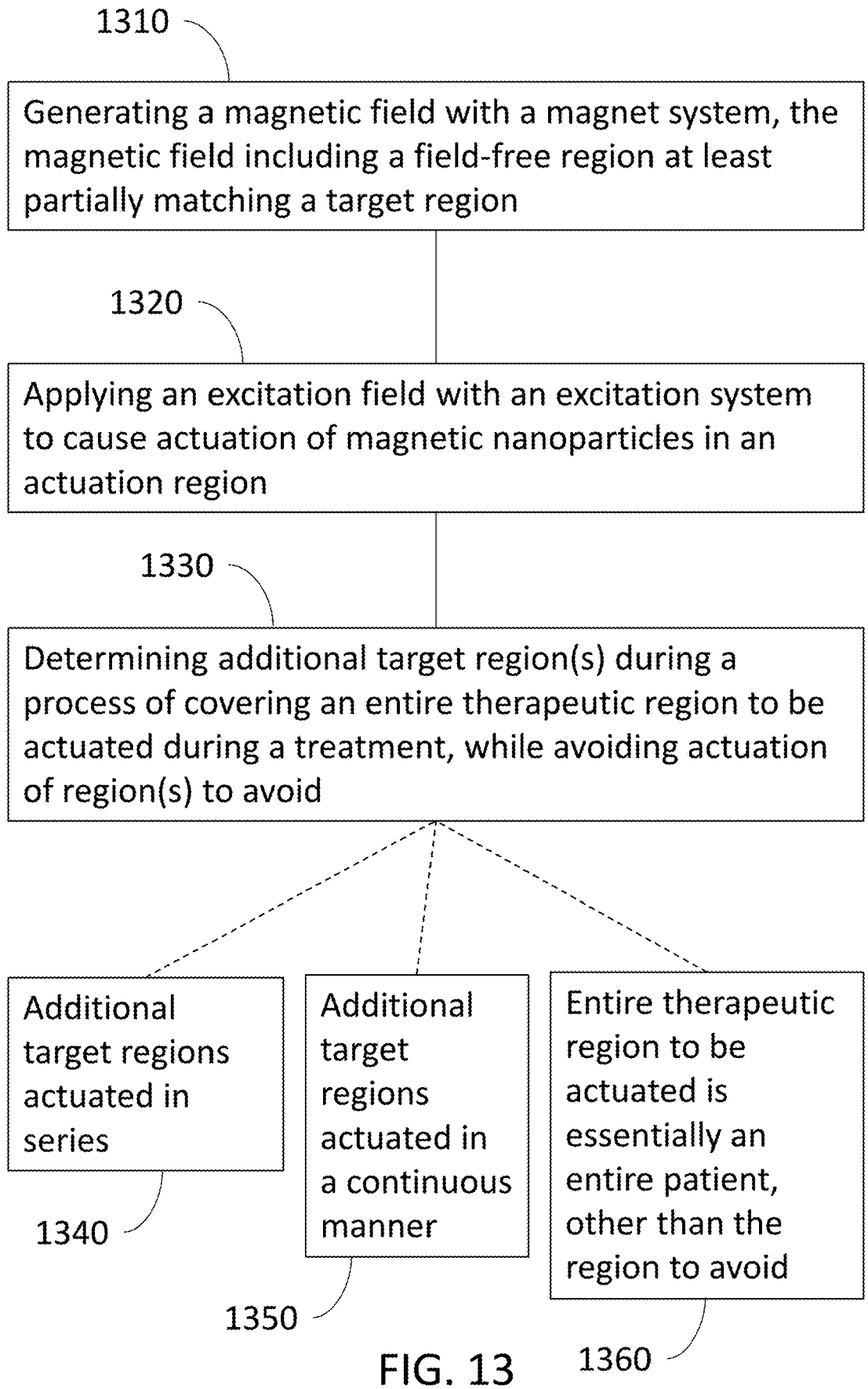
FIG. 13 is a diagram illustrating an exemplary process for FFR matching to a target region and actuation of magnetic nanoparticles in accordance with certain aspects of the present disclosure.

Any combination of the disclosed methods of shaping the FFR to at least partially match the target region and actuating MNPs in an actuation region can be implemented by computer software and corresponding magnet systems, excitation systems, and control systems as described herein. For example, as illustrated in FIG. 13, at 1310, computer operations can include generating a magnetic field with a magnet system, the magnetic field including a field-free region at least partially matching a target region.

At 1320, an excitation field can be applied with an excitation system to cause actuation of magnetic nanoparticles in an actuation region.

Other embodiments can include additional operations, for example, at 1330, the operations can further include determining additional target region(s) during a process of covering an entire therapeutic region to be actuated during a treatment, while avoiding actuation of region(s) to avoid.

Also, the operations can optionally include, at 1340, actuating additional target regions in series, at 1350, actuating additional target regions in a continuous manner, or at 1360, causing an entire therapeutic region to be actuated to be essentially the entire patient other than the region to avoid.

To localize RF actuation of nanoparticles with high spatial resolution in a patient, one or more FFRs can be generated using magnet systems as disclosed herein. Implementations of the magnet system can be configured to change the size, shape, rotation and/or location of the one or more FFRs, as previously discussed.

Figure 14:
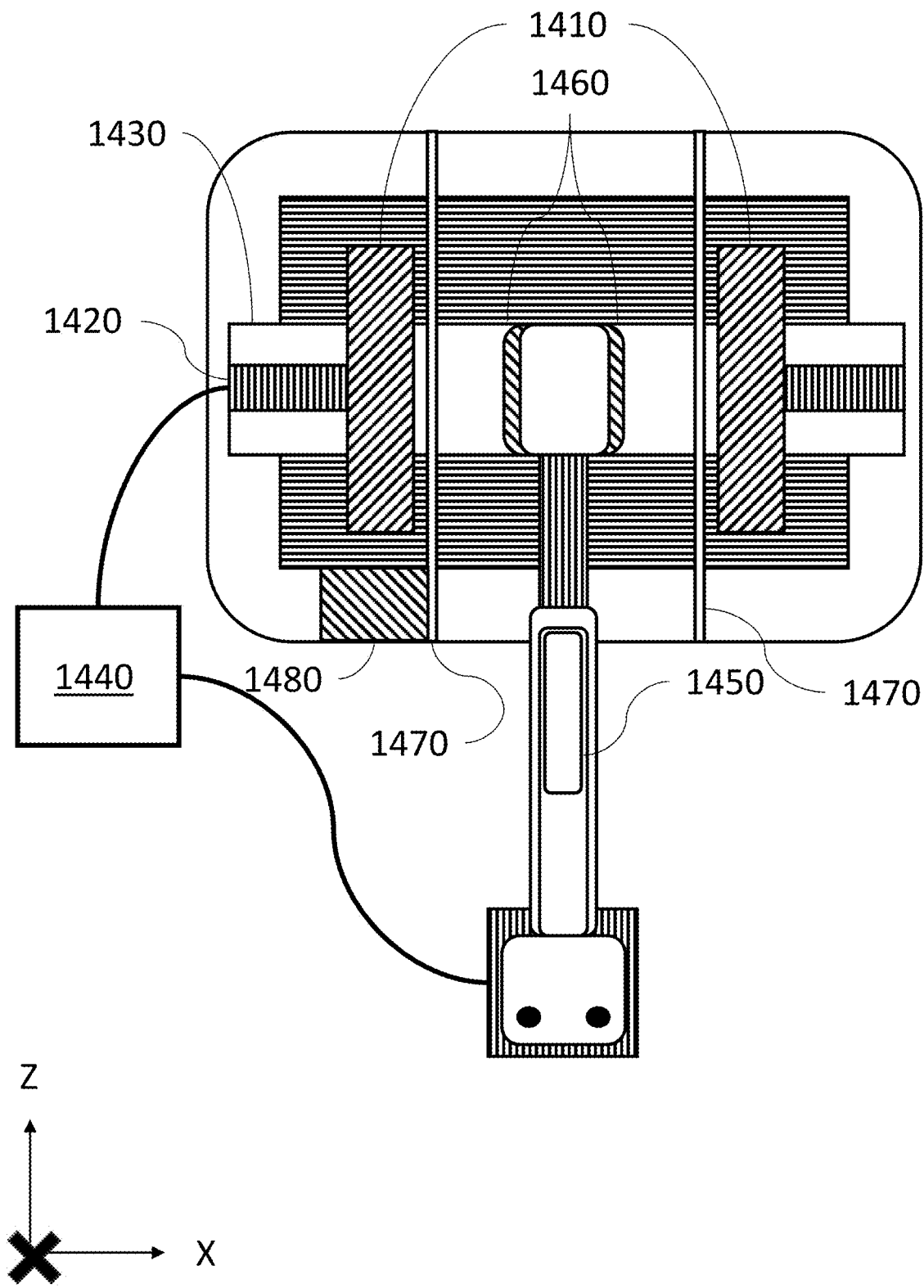
FIG. 14 is a diagram illustrating a simplified top view of an exemplary magnetic particle actuating system with a first magnet set in accordance with certain aspects of the present disclosure.

FIG. 14 illustrates one example of such a magnetic particle actuating system. The magnetic particle actuating system can include a magnet system configured to generate a magnetic field that includes an FFR. The magnet system can include magnetic materials and/or electromagnets, with a first set of magnets 1410 shown in FIG. 14. As used herein, "magnetic materials" include permanently magnetized materials (permanent magnets), non-permanently magnetized materials (e.g., ferromagnetic materials such as iron, steel, and nickel), or ferrimagnetic materials (e.g., yittrium iron garnet, aluminum, cobalt, nickel, etc.). As used herein, the term "magnet" can refer to permanent magnets or electromagnets.

The magnet system can also include associated mechanical support structures and one or more control systems that can encompass any mechanical/electrical mechanisms for translating, rotating, moving, or operating of any of the components of the magnet system or excitation system. FIG. 14 illustrates simplified representations of stage systems for moving one or more components of the magnet system. For example, as discussed further below, stage systems can include an X-axis stage 1420 and/or a Y-axis stage 1430, as well as other stages for further translations or rotation of components of the magnet system.

A control system 1440 can be configured to control the magnet system to create a field-free region at least partially matching a target region. The at least partially matching of the field-free region to the target region can include causing mechanical movement of one or more magnets or magnetic materials in the magnet system to translate, scale, rotate, or change the shape of the field-free region. The control system can be further configured to control the magnet system to cause the field-free region to enclose a target region, conform to the target region, or avoid overlap with a region to avoid.

Additionally, the control system can be configured to determine additional target region(s) for a process of covering an entire therapeutic region to be actuated during a treatment, while avoiding actuation of a region to avoid, to actuate the additional target regions in series, to actuate the additional target regions in a continuous manner, or to actuate essentially an entire patient, other than the region to avoid.

To provide support for and positioning of the patient in the magnetic actuation system, a patient couch 1450 can be provided. The patient couch can allow for movement of the patient into the bore of the magnetic actuation system where the FFR will be generated. As further discussed below, the patient couch can be connected to the control system for controlling the relative position between the patient (and the target regions therein) and the FFR.

Other elements illustrated in FIG. 14 and discussed herein include components 1460 of an RF excitation system and shielding 1470 between the RF excitation system and the magnet system. Optionally, sensors 1480 such as thermal probe sensors or other devices configured to monitor the effects of MNP actuation can be included in the magnetic actuation system.

Figure 15:
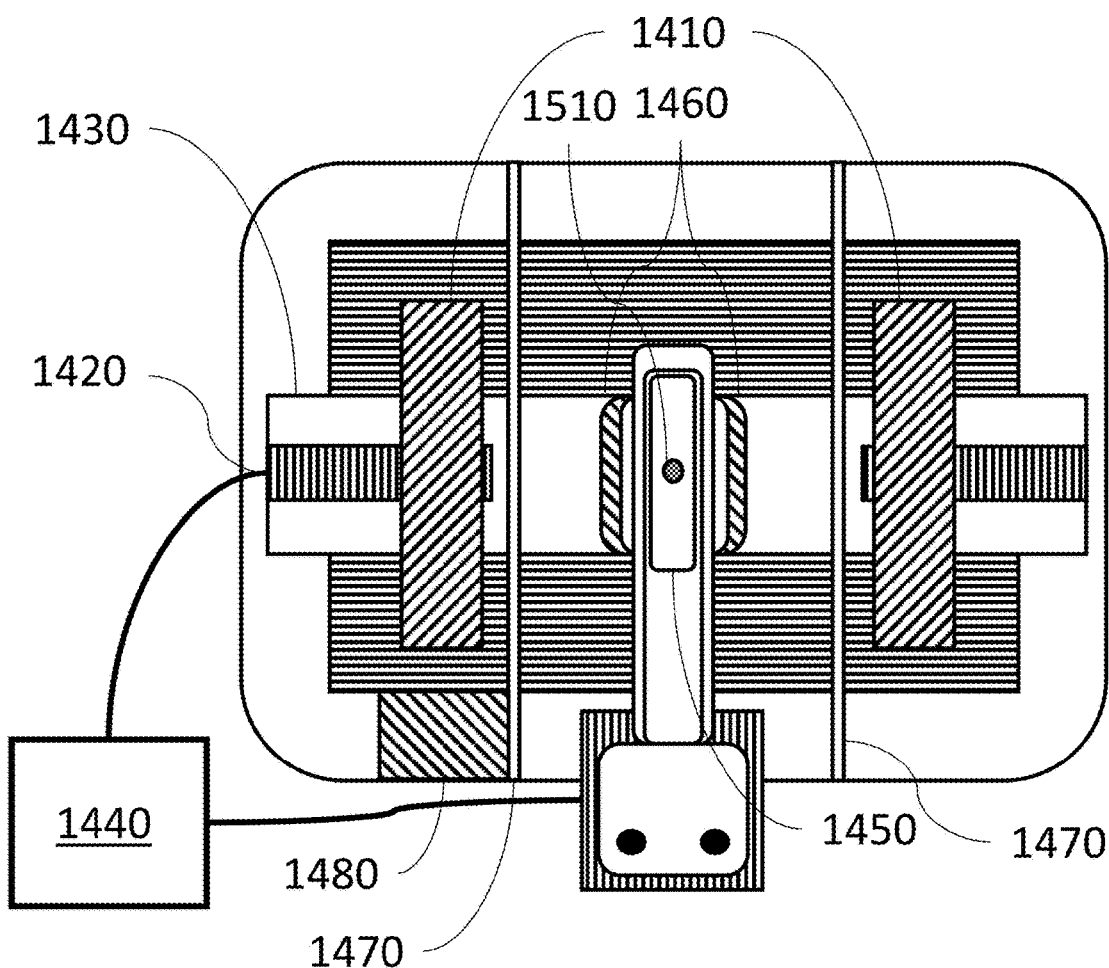
FIG. 15 is a diagram illustrating an exemplary generation of a FFR in the magnetic particle actuating system of FIG. 14 in accordance with certain aspects of the present disclosure.
Figure 15:
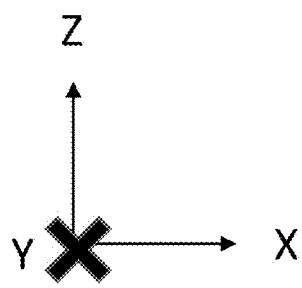
Figure 16:
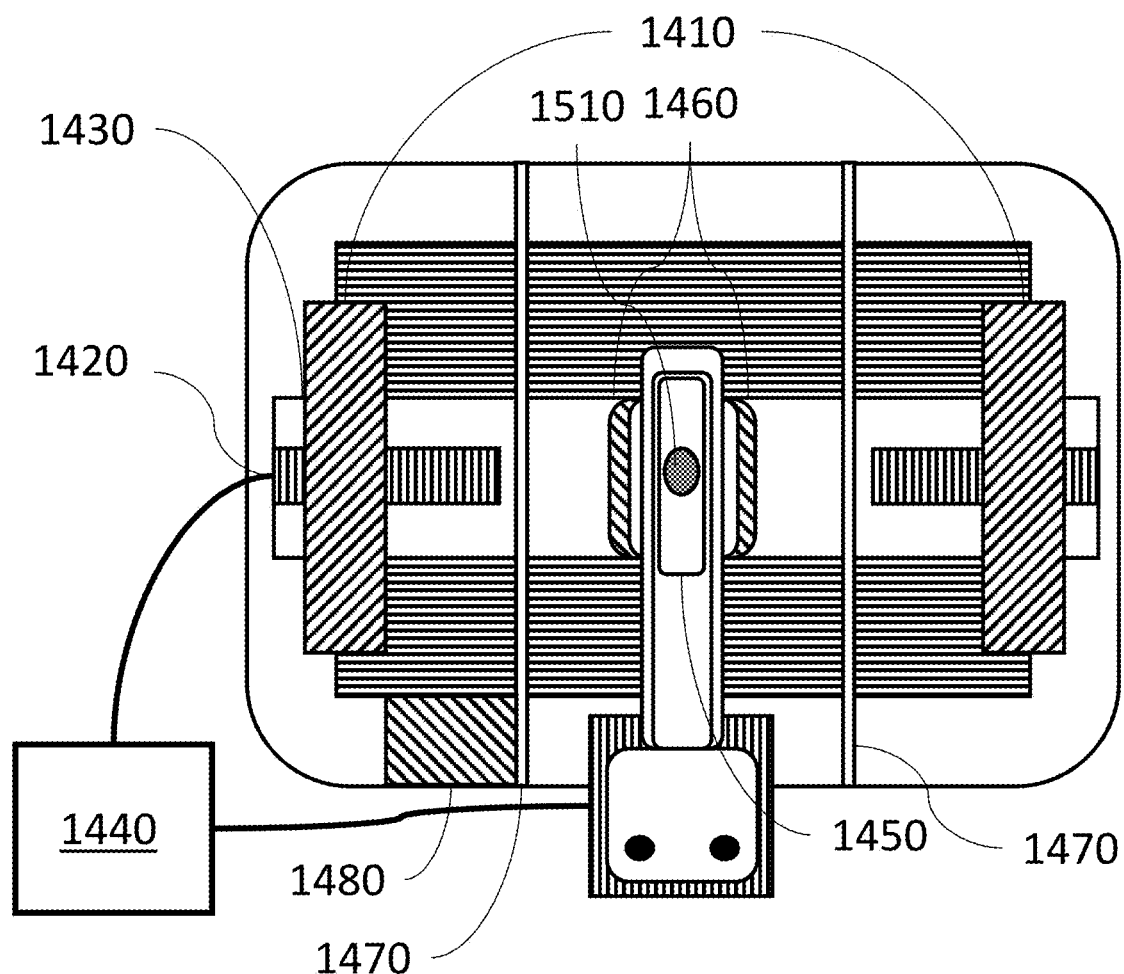
FIG. 16 is a diagram illustrating an exemplary changing the size of a FFR in the magnetic particle actuating system of FIG. 14 in accordance with certain aspects of the present disclosure.
Figure 16:
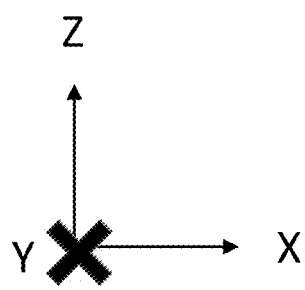
Figure 17:
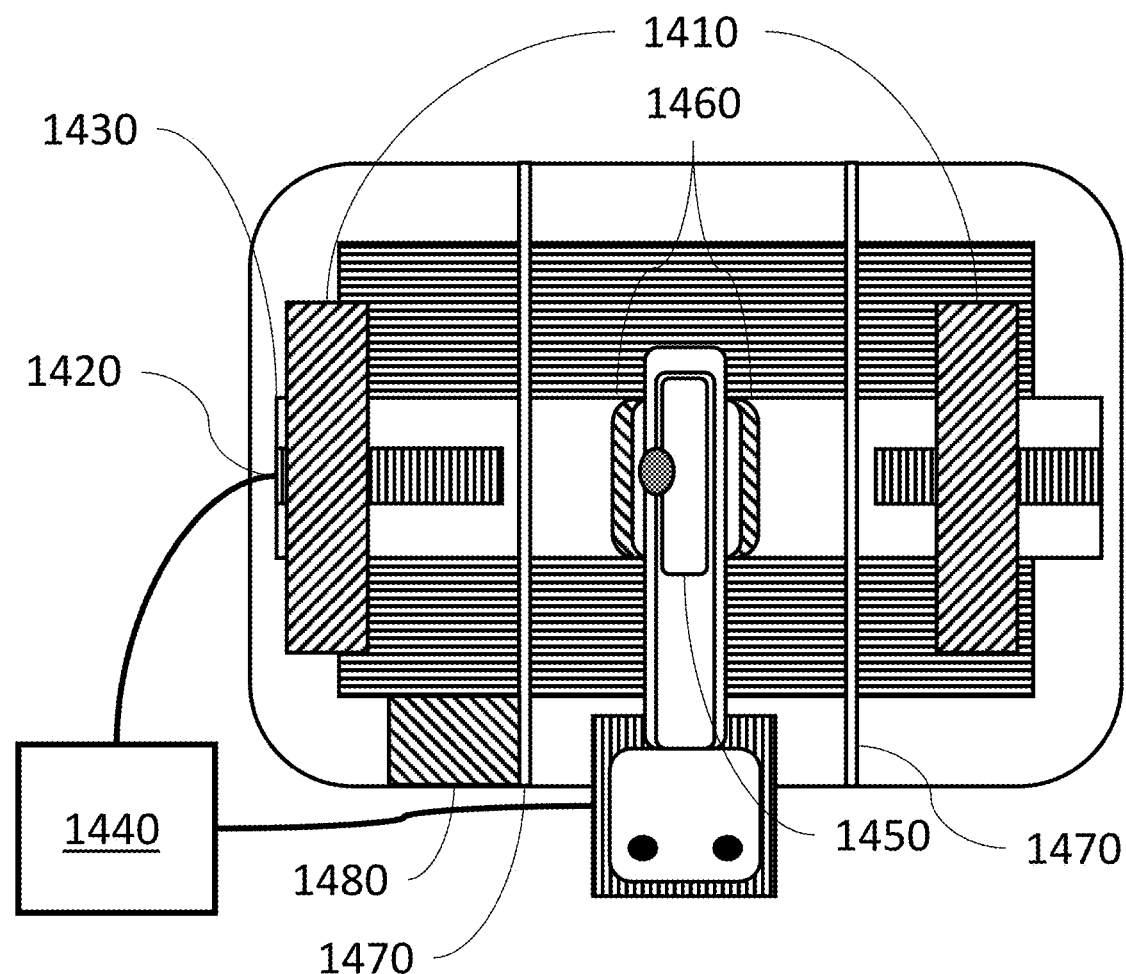
FIG. 17 is a diagram illustrating an exemplary translating and changing the size of a FFR in the magnetic particle actuating system of FIG. 14 in accordance with certain aspects of the present disclosure.

As shown in FIGS. 15-17, the magnet system can include a first set of magnets 1410 on either side of the field-free region. This first set of magnets can be controlled to, for example, translate or change the shape of the FFR. FIG. 15 illustrates a simplified FFR 1510 located approximately at the center of the magnetic actuation system and created by the pair of magnets 1410 that are of equal magnetic strength.

FIG. 16 illustrates a simplified representation of the effect of translating outward both magnets of the first set of magnets. Here, FFR 1510 increases in size due to the reduced gradient field strength produced by the magnetic actuation system. When only one magnet is translated, as illustrated in FIG. 17 by the left magnet having moved outward, this causes two effects on the FFR. First, FFR 1510 increases in size from the increased separation between the magnets, similar to the increase in size shown in FIG. 16. Second, FFR 1510 translates to the left due to the change in the location of the magnetic null between the two magnets.

This simplified example illustrates how the movement of magnets can cause multiple effects in the sizing and location of the FFR.

Accordingly, the at least partial matching of the field-free region to the target region can include independently controlling at least one of a first set of magnets to translate along a first axis (shown in FIGS. 15-17 as being the X axis). The translation can be implemented by a first magnet stage system configured to independently translate at least one of the first set of magnets along the first axis. In this way, the control system can then be further configured to control at least one of the first set of magnets to translate along the first axis as part of the at least partial matching of the field free region to the target region.

Furthermore, the first magnet stage system can be configured to independently translate along a second axis (e.g., up and down along the Y axis). Accordingly, the control system can be further configured to cause mechanical translation of the first set of magnets along a second axis as part of the at least partial matching of the field-free region to the target region.

As noted, the system can also include a patient couch. The control system can be further configured to control reorientation of the patient couch as part of the at least partial matching of the field-free region to the target region. As shown in FIGS. 14-17, the patient couch may be introduced into a magnet-free region (e.g., the bore) with a translation mechanism such as a linear stage. Additionally, the magnet system and/or the translation mechanism(s) can adjust the relative positioning between the patient and one or more FFRs to, for example, improve the matching of the FFR for actuation of MNPs.

Figure 18:
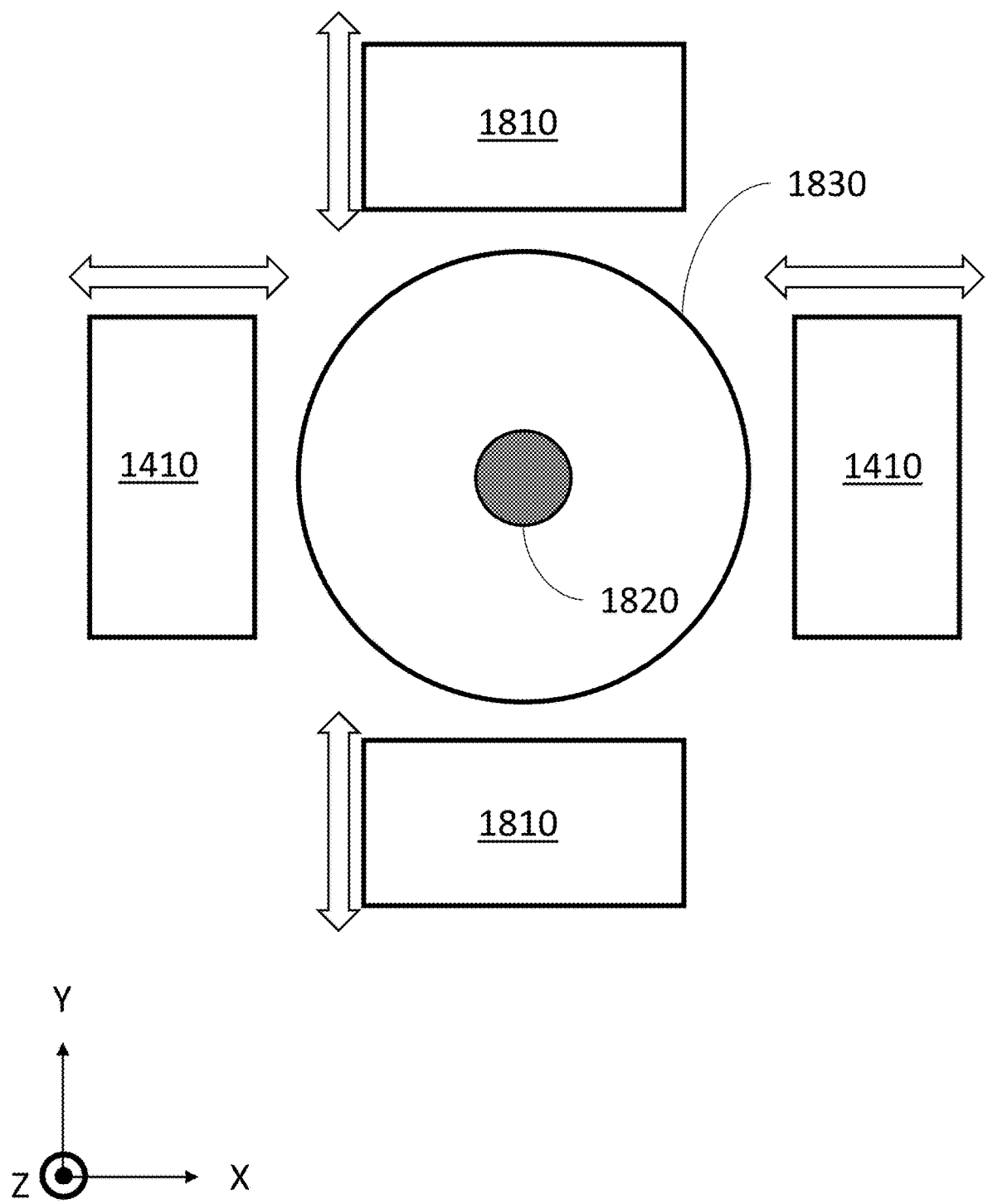
FIG. 18 is a diagram illustrating a simplified front view of an exemplary magnetic particle actuating system adding a second magnet set in accordance with certain aspects of the present disclosure.

Additional control over the shape and placement of the FFR can be achieved by including additional magnets, for example, as in the implementation illustrated in FIG. 18 showing a simplified front view of the magnetic particle actuation system. In this implementation, the magnet system further includes a second set of magnets 1810 on either side of field-free region 1820 (e.g., above and below the center of the magnetic particle actuation system). As shown in FIG. 18, first set of magnets 1410 and second set of magnets 1810 can be disposed outside bore 1830. There can also be a second magnet stage system configured to independently translate at least one of the second set of magnets along a second axis (e.g., up and down along the Y-axis as shown in FIG. 18). The control system can be further configured to control at least one of the second set of magnets to translate along the second axis as part of the at least partial matching of the field-free region to the target region. This second set of magnets allows additional degrees of freedom for manipulating the shape or location of the FFR, similar to what was previously shown in FIGS. 14-17.

Figure 19:
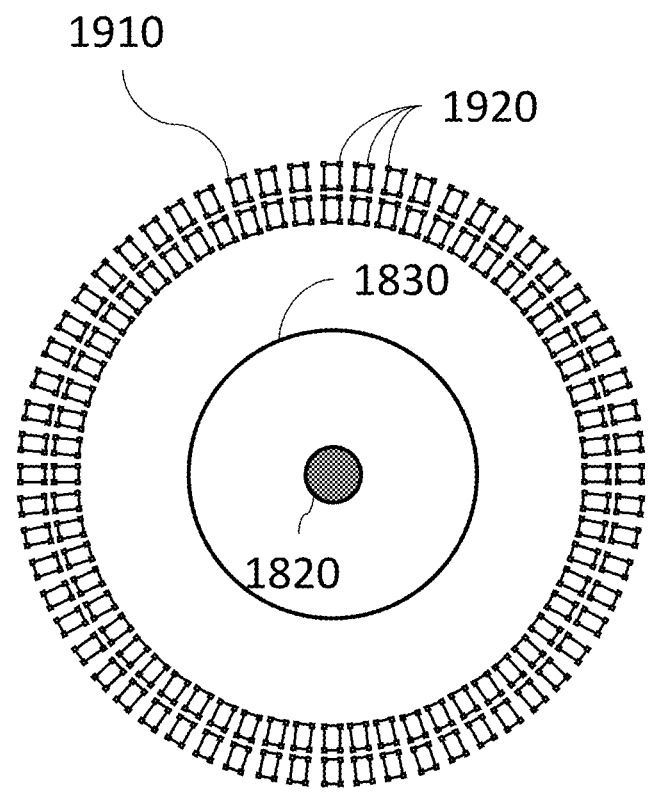
FIG. 19 is a diagram illustrating a simplified front view of an exemplary Halbach array in accordance with certain aspects of the present disclosure.
Figure 19:
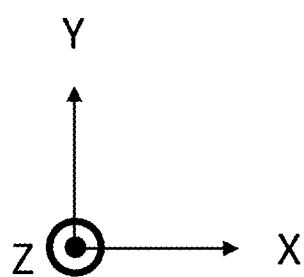
Figure 20:
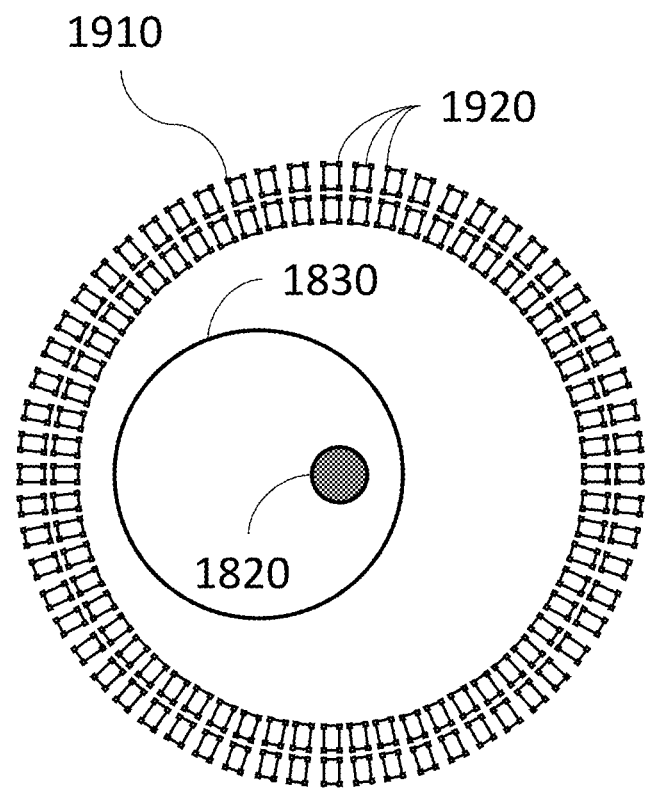
FIG. 20 is a diagram illustrating a simplified front view of translated a Halbach array in accordance with certain aspects of the present disclosure.
Figure 20:
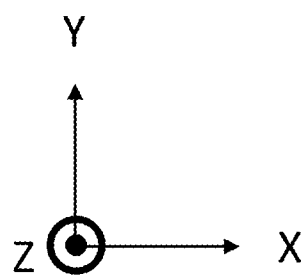

Still further manipulation of the FFR can be achieved by, for example, inclusion of an array of radially oriented magnetic materials. In particular, FIG. 19 shows one example of a Halbach array 1910 having magnetic materials 1920 (e.g., a generally circularly oriented array of magnets). In some implementations, a Halbach array can include permanent magnets, electromagnets, and/or ferromagnetic material such as iron to assist with forming a desired FFR. Additionally, as illustrated in FIG. 20, the Halbach array can be translated similar to the previously described magnet sets. And similar to the previously described magnet sets, such translation can cause a translation of the FFR.

In yet other implementations, the control system can be further configured to move one or more of the magnetic materials to a specified radial distance as part of the at least partial matching of the field-free region to the target region. For example, any of the magnets of the Halbach array can be coupled to a radial drive to provide for this independent movement. In this manner, the FFR may be shaped asymmetrically and/or multiple distinct/disjointed FFRs can be created.

In addition to being capable of independent radial movement, elements of the Halbach array can be configured to move together to allow, for example, a more symmetrical change in the size and shape of the FFR (as compared to the linear stage magnets discussed above). In some implementations, the magnetic materials in the Halbach array can be disposed in a circular configuration having a diameter. Accordingly, the control system can be further configured to control the plurality of magnetic materials to move radially to change the diameter of the Halbach array as part of the at least partial matching of the field-free region to the target region.

In some implementations, the magnet system can include one or more electromagnets and the at least partially matching the field-free region to the target region can be based at least on controlling current(s) in the one or more electromagnets. In systems comprising one or more electromagnets, the electromagnets may be used to electronically shift the location/shape of the FFR in place of, or in combination with mechanical movement of the magnets.

Figure 21:
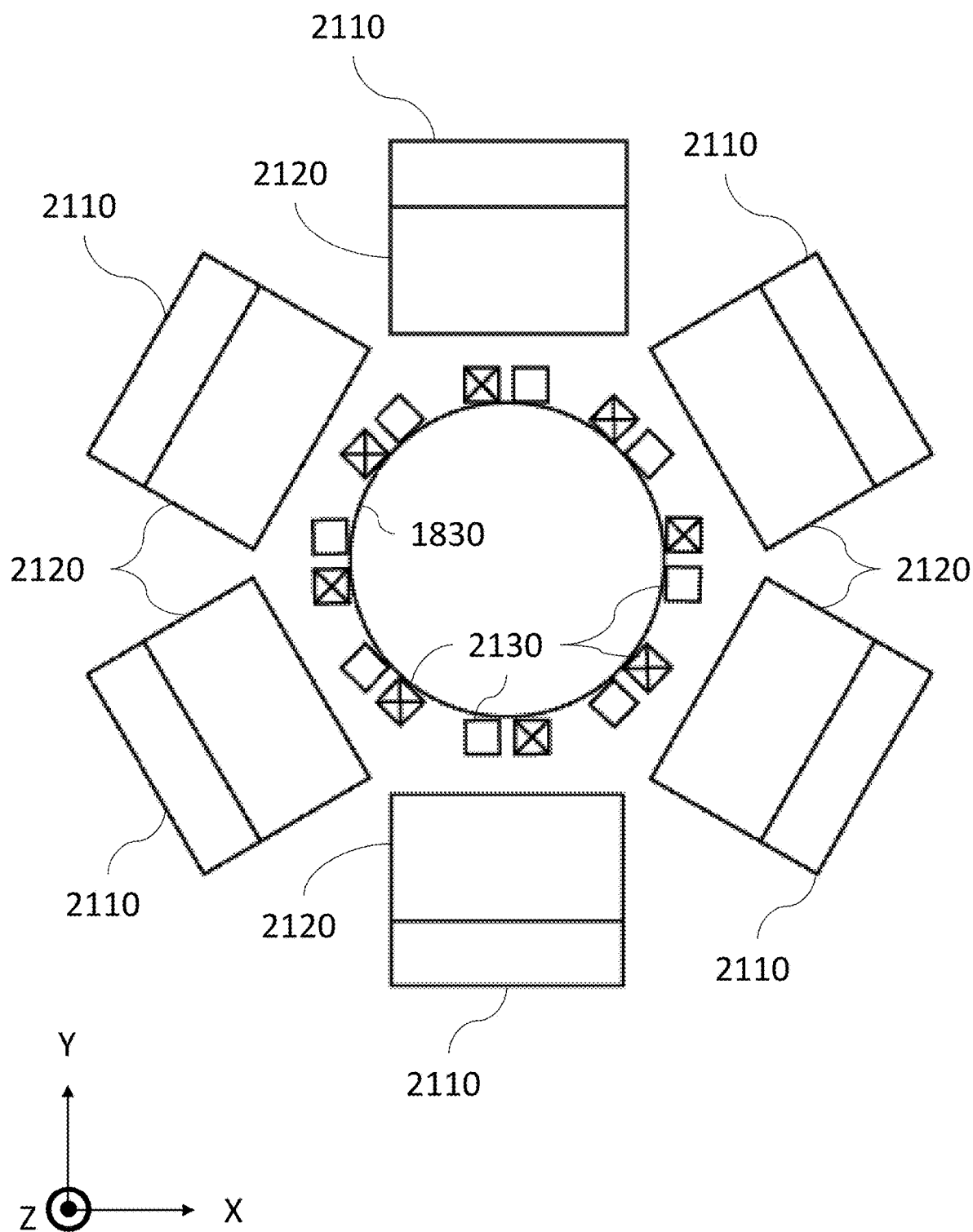
FIG. 21 is a diagram illustrating a simplified front view of an exemplary magnetic particle actuating system combining permanent magnets, non-permanently magnetized magnetic materials, and electromagnets in accordance with certain aspects of the present disclosure.

The above magnet systems can be combined in various geometries and locations to provide high-resolution, multidimensional control over the FFR. For example, as shown by the embodiment illustrated in FIG. 21, the magnet system can include one or more permanent magnets 2110, one or more magnetic materials 2120, and one or more electromagnets 2130. Here, the different magnet types are arranged at different radial distances from the center of the bore. However, this is intended to be an example only and as such the location, number, and radial order of any of the magnets can be varied.

Figure 22:
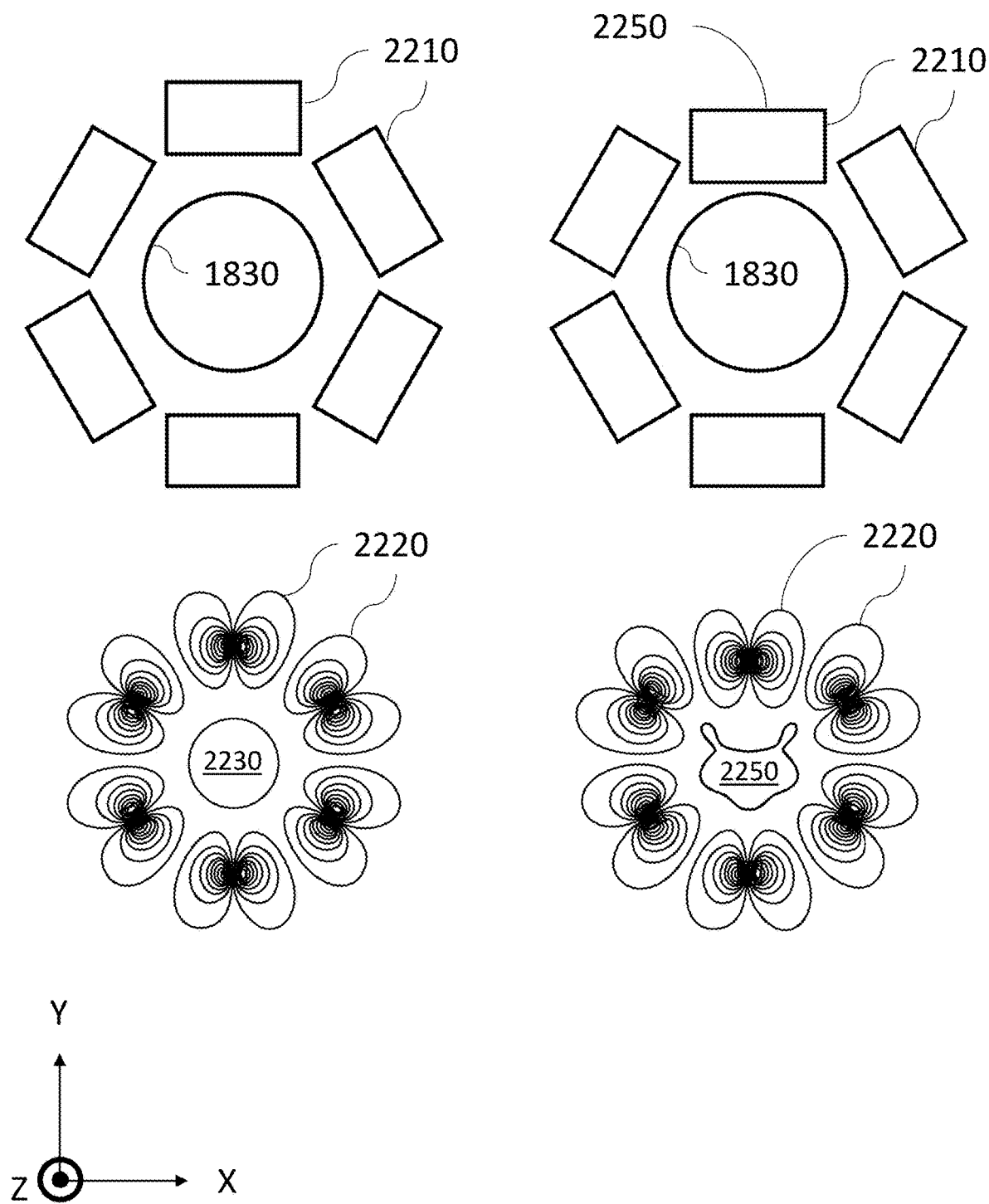
FIG. 22 is a diagram illustrating a simplified front view of an exemplary magnetic particle actuating system with a magnet translated to change the shape of the FFR in accordance with certain aspects of the present disclosure.

The control system can be further configured to cause mechanical movement of the one or more permanent magnets and cause mechanical movement of one or more magnetic materials that is not permanently magnetized and control current(s) in the one or more electromagnets to translate, scale, rotate, or change the shape of the field-free region. FIG. 22 illustrates an example of how just a simple translation of such a magnet system can result in a complex FFR. The upper left illustration in figure FIG. 22 shows a simplified arrangement of six magnets 2210 disposed symmetrically around bore 1830. Below it, is a simplified illustration of magnetic field lobes 2220 generated by such magnets. In the center of the lower left illustration is a depiction of a resultant FFR 2230 having a circular shape in the X-Y plane (due to the symmetry of the magnet configuration). The upper right illustration shows the top magnet 2250 translated radially inward. Below that illustration is a depiction of the resultant magnetic field lobes 2220 and new FFR 2250, having a significantly more complex shape.

Active excitation, energy deposition, or actuation of magnetic nanoparticles can be achieved via radiofrequency (RF) fields. RF coils can be designed to generate the desired fields with a geometry specified in terms of the coil sensitivity and the theory of reciprocity. In some embodiments, RF coils will be designed to provide a substantially spatially homogeneous field over some field-of-view (FOV).

While an FFR created by the magnet system (as described above) can provide a powerful actuation-localization mechanism, RF coil sensitivity profiles can also be used to shape energy deposition. The combination of specialized RF coil sensitivity localization and FFR localization can thus provide an unprecedented degree of spatial targeting in RF actuation.

An excitation field can be applied through an excitation system that can include one or more RF coils. In one implementation, the magnetic particle actuating system can include a single RF coil. Accordingly, the control system can be further configured to generate the excitation field with the single RF coil. In other implementations, the excitation system can include at least one spatially inhomogeneous RF coil and the control system can be further configured to generate the excitation field utilizing the at least one spatially inhomogeneous RF coil.

In other embodiments, the excitation system can include multiple RF coils that can be independently controllable. For example, a solenoid RF coil circumscribing the magnet-free region may provide excitation with a field vector oriented perpendicular to the circular cross-section of the coil and RF saddle coils may provide excitation with a field vector oriented along the remaining perpendicular spatial directions. As such, the control system can be further configured to cause the excitation field to be generated along multiple axes utilizing the multiple independently controllable RF coils, including utilizing the solenoidal RF coil and the multiple saddle RF coils.

As described herein, the excitation field can be generated in a manner that changes the actuation region. In the presence of an FFR, a spatially homogeneous AC RF field will rapidly move the FFR over some distance. Actuation of MNPs will occur along the length of the FFR path, or said another way, throughout the volume the FFR passes through over the course of RF oscillations. Therefore, RF amplitude and vector trajectory will also influence the spatial localization of RF actuation in addition to the means of generating and shaping an FFR (statically or with low-frequency dynamics) and the use of spatially inhomogeneous coils previously discussed. Furthermore, while a spatially homogeneous AC field shifts an FFR, an inhomogeneous AC field will both spatially distort and shift the FFR.

Figure 23:
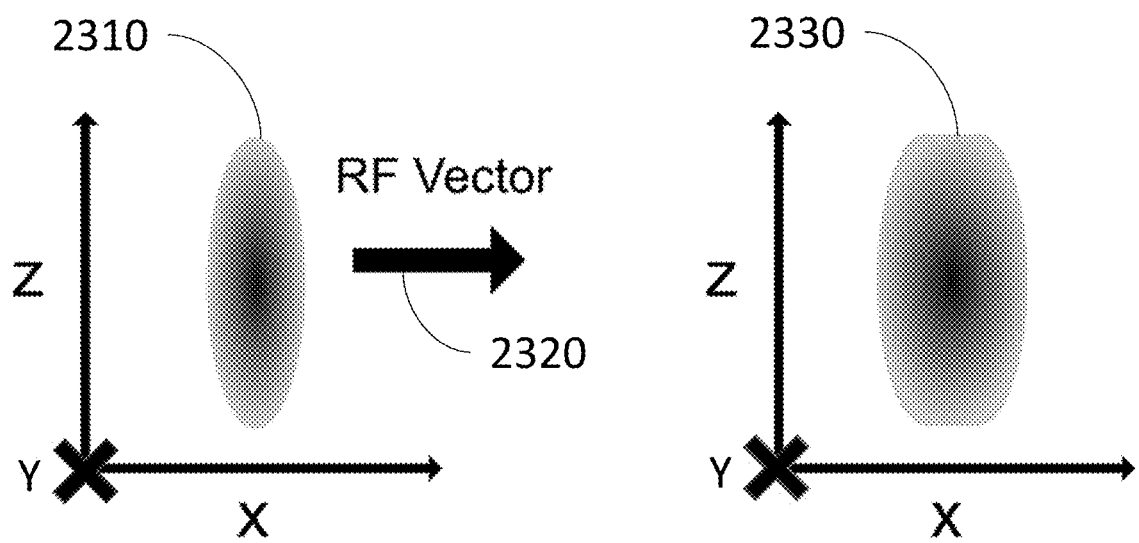
FIG. 23 is a diagram illustrating an exemplary application of an RF field on a vector along an X axis, which during actuation rapidly oscillates an FFR along the vector path, leading to an actuation region that encompasses the full volume impinged by the FFR during actuation, in accordance with certain aspects of the present disclosure.
Figure 24:
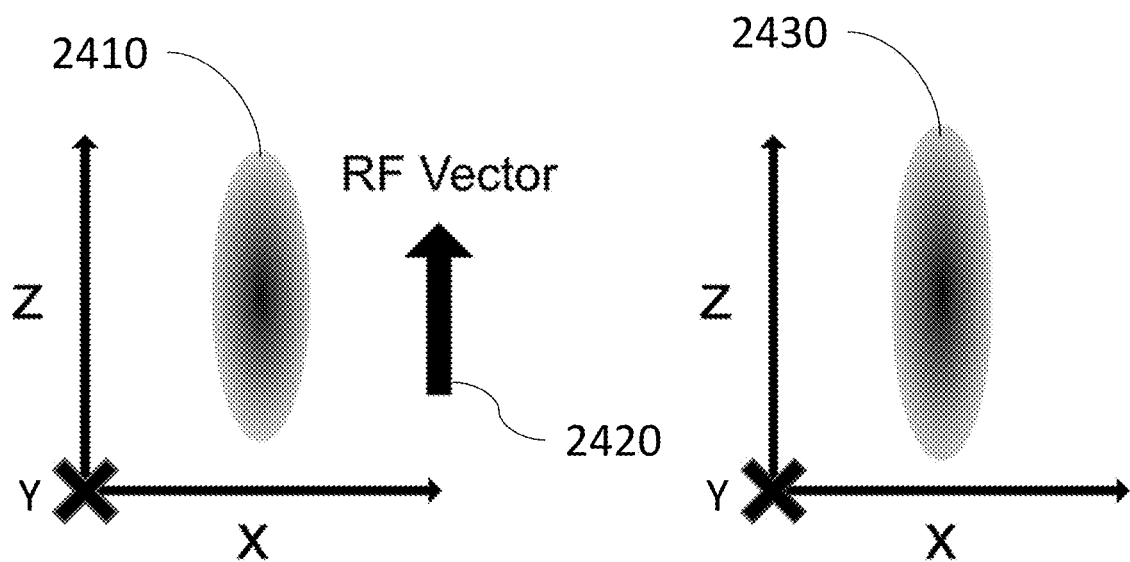
FIG. 24 is a diagram illustrating an exemplary application of an RF field on a vector along a Y axis, which during actuation rapidly oscillates an FFR along the vector path, leading to an actuation region that encompasses the full volume impinged by the FFR during actuation, in accordance with certain aspects of the present disclosure.
Figure 25:
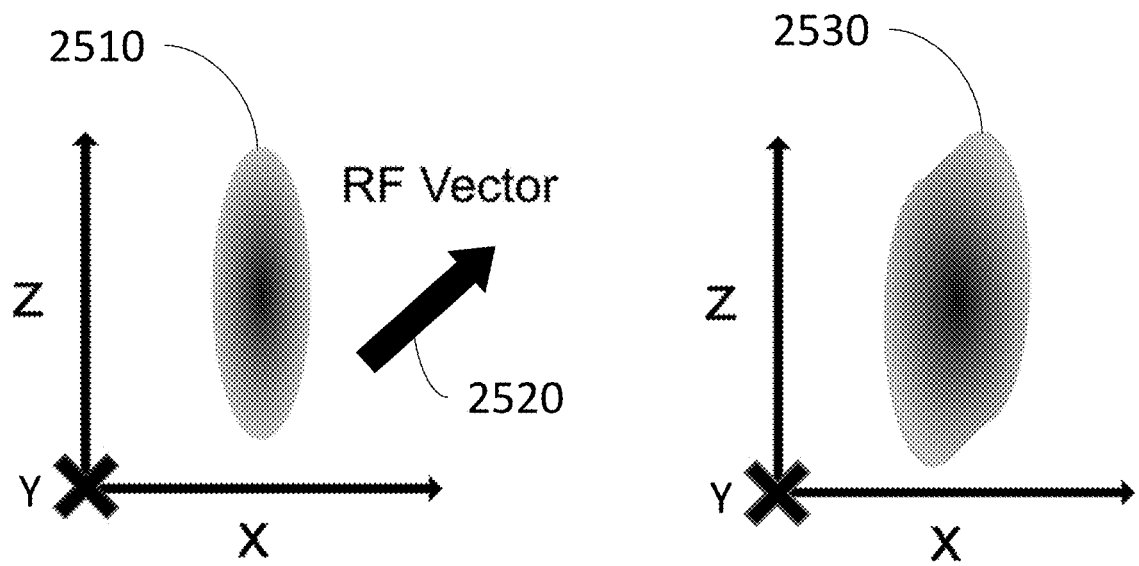
FIG. 25 is a diagram illustrating an exemplary application of an RF field on a vector with components along an X axis and Y axis, which during actuation rapidly oscillates an FFR along the vector path, leading to an actuation region that encompasses the full volume impinged by the FFR during actuation, in accordance with certain aspects of the present disclosure.

Simplified examples of the effect of RF vectors are illustrated in FIGS. 23-25. The left portion of each figure illustrates FFR 2310, 2410, 2510. In FIG. 23, an arrow indicates an RF vector 2320 oriented along the X-axis. The right figure shows the effect of the excitation field on the actuation region. Here, because the RF vector was in the X direction, the FFR is oscillated along the X-axis such that over this time the FFR sweeps through a volume forming the shape of actuation region 2330. FIG. 24 illustrates a similar effect on FFR 2410 but for an RF vector 2420 in the Y direction. Similarly, actuation region 2430 is extended some distance along the Y-axis. FIG. 25 illustrates yet another example where RF vector 2520 has components in both the X and Y directions. Accordingly, FFR 2510 is oscillated in the direction of RF vector 2520 based on those vector components to form actuation region 2530.

Based on the abilities of certain excitation systems disclosed herein, the control system can thus be further configured to control multiple independently controllable RF coils to allow selection of the RF vector along which the actuation region is changed through specifying currents through the multiple independently controllable RF coils. In some implementations, the multiple independently controllable RF coils are configured to be controllable (e.g., by the control system) to change a magnitude of the RF vector through specifying currents through the multiple independently controllable RF coils. FIGS. 23-25 are only exemplary cases meant for illustrative purposes. In general, the geometrical difference between the actuation region and the FFR can depend on a number of factors, such as excitation amplitude, vector direction (shown in the figures), tracer magnetization curve, and actuation physics.

Body part-specific RF coils may be designed to make contact with the subject and means of cooling the coil or the coil-tissue interface may be provided. For example, a thin, water-perfused interface may separate a dedicated RF coil and a body part such as a head or a breast.

Figure 26:
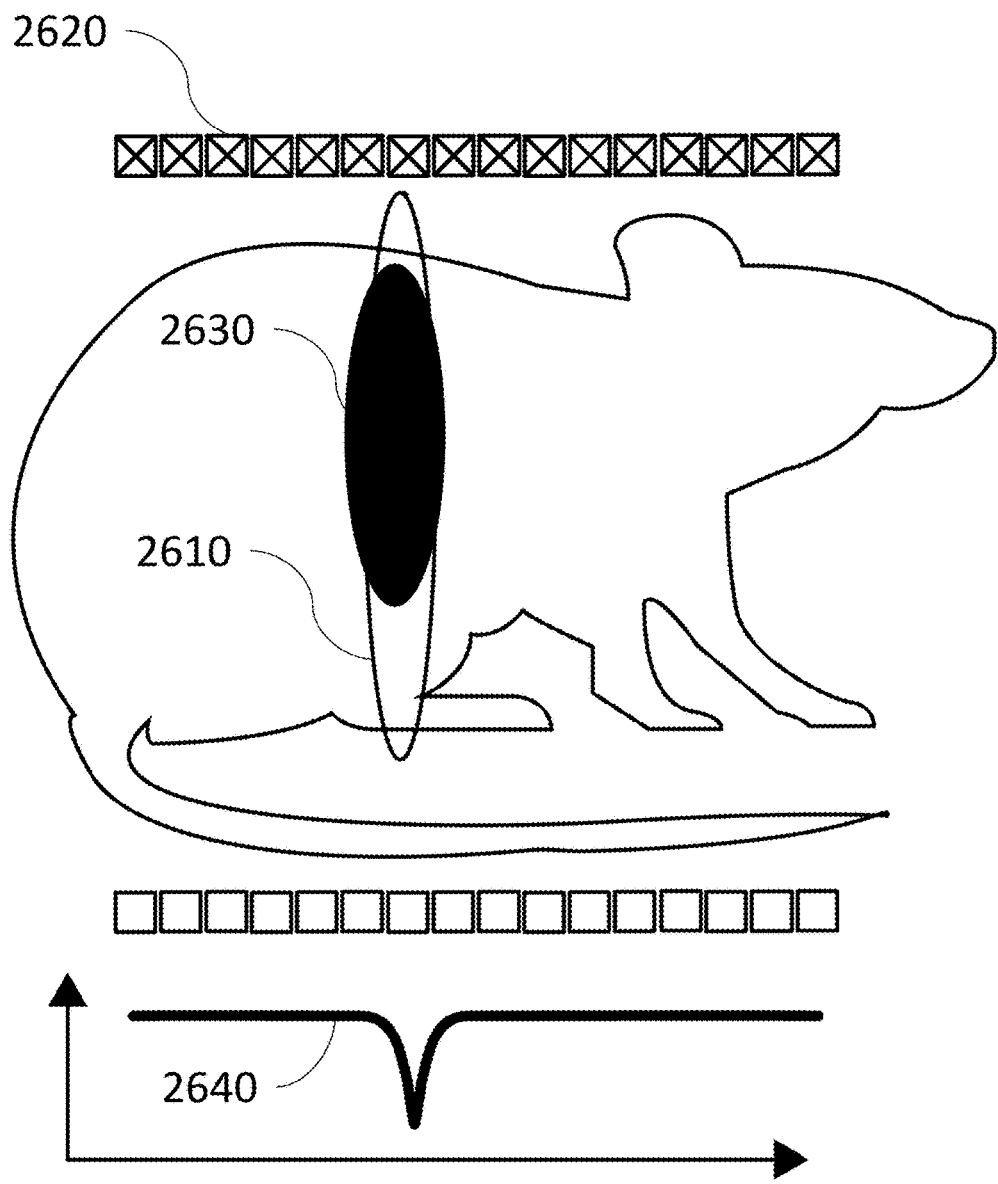
FIG. 26 is a diagram illustrating a side view of an exemplary wire loop in accordance with certain aspects of the present disclosure.

Other implementations of the current subject matter allow for a tailoring of the excitation field that reaches the patient by attenuating or blocking at least some of the RF emitted from the RF coils. For example, the magnetic particle actuating system can include a passive component. FIG. 26 illustrates one example of a passive component being a wire loop that acts to attenuate the delivered excitation field to the target. Essentially, the wire loop shown at a particular location along the patient causes the RF excitation field generated by RF coils 2620 to deposit a portion of their energy into the wire loop and drive a current around it. The current induced in the coil or wire loop then locally reduces the magnetic field so that less energy is transmitted to the patient in that location. In some implementations, wire loop may be a shorted wire loop that is shorted to ground or otherwise able to electrically discharge the induced current in the wire loop. The bottom of the figure shows an example representation of amplitude 2640 of RF reaching the patient. Here, the plot shows the localized reduction in excitation field amplitude at the location of the wire loop, which is positioned around region to avoid 2630. It is contemplated that the control system can be further configured to cause placement of the passive component to shape the excitation field, for example to avoid actuation of the region to avoid. In this way, the control system can be configured to instruct the magnetic particle actuator system to move the passive component to a particular location and/or move the patient couch to the location of the passive component.

Implementations of the magnetic particle actuating systems herein may further include an RF shield disposed between a portion of the excitation system and a portion of the magnet system (and possibly the external environment) to reduce interference of the excitation system during the generation of the excitation field. One example of such was illustrated in FIGS. 14-17. The RF shield can be, for example, a tube made of copper, steel, aluminum, or similarly suitable conductive material. In FIG. 14, distinct plates are used instead of a continuous tube/enclosed construct. In some implementations, the portion of the excitation system inside the RF shield can include one or more RF coils. The portion of the magnet system outside the RF shield can include one or more magnets of the magnet system. In other implementations, the magnetic particle actuating system can include one or more RF receiver coils, where the RF shield can be disposed between the one or more RF receiver coils and the portion of the magnet system. The RF shield can be configured to reduce interference to or from external sources (e.g., aspects of the magnet system, AM radio, other nearby RF generating equipment, etc.), for example, by being of sufficient thickness to shield against electromagnetic fields at an interfering frequency. In other implementations, the RF shield can prevent detuning of the transmit coil as the magnets are moved mechanically. In general, the RF shield can be designed with such a thickness as to block interferers in a sensitive range (e.g., encompassing the fundamental excitation frequency and possibly some number of harmonics of the fundamental excitation frequency), while passing low-frequency magnetic fields, e.g., electromagnetic fields of the magnet system that translate/shape the FFR during operation. Such low-frequency magnetic fields can be, for example, approximately 1, 5, 10, 25, 50, 75, or 100 Hz.

Figure 27:
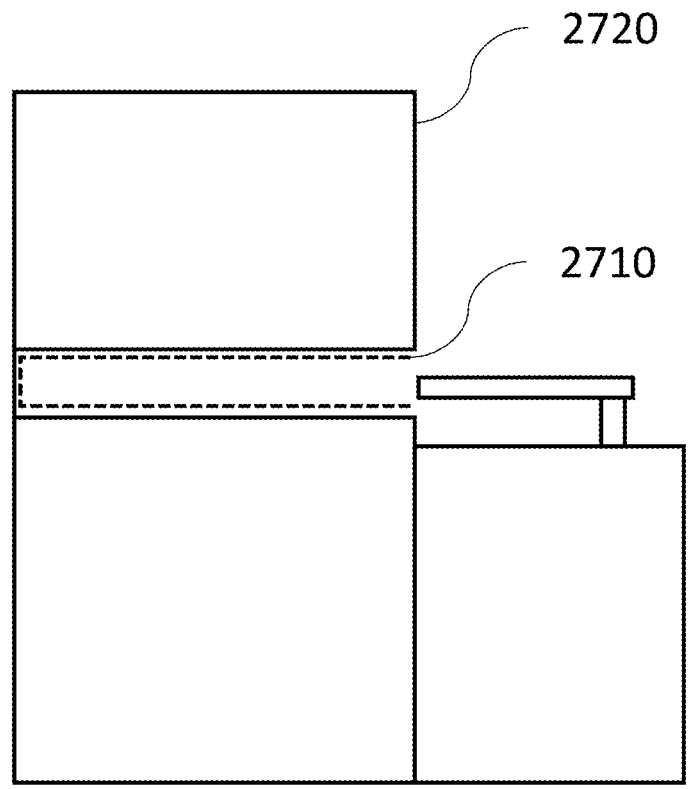
FIG. 27 is a diagram illustrating a side sectional view of an exemplary magnetic particle actuating system including a swappable cassette in accordance with certain aspects of the present disclosure.

The magnetic particle actuator systems disclosed herein can be used across a broad application spectrum. Accordingly, the desired performance characteristics, including desired resonant frequency, desired field strengths, and degree of spatial localization can vary widely. Therefore, the excitation system can include a swappable cassette 2710 containing at least a portion of the excitation system. A simplified example of a system that includes the swappable cassette is illustrated in FIG. 27. The swappable cassette can be easily exchanged in magnetic particle actuating system 2720 with other swappable cassettes having different configurations of RF generating components. Portions of the excitation system in the swappable cassette can include resonators that enable the desired performance characteristics. Resonators of different cassettes may differ in various important metrics such as geometry and form factor, resonant frequency, coil diameter, coil inductance, impedance, cooling strategies employed, and interaction level with the subject (e.g., contact and non-contact).

The RF coils and elements of high-powered resonator circuits, such as the matching capacitors, may be actively cooled. In some embodiments, thermal fluids such as water or oil may perfuse hollow coil wiring. In other embodiments, thermal fluids bathe coils and other components placed in an enclosed thermal circuit. In other embodiments, solid heat sinks may be attached with high conductivity materials to components such as the matching capacitors. These heat sinks may be actively or passively cooled. In some embodiments, various thermal mitigation mechanisms are used simultaneously. In some embodiments, the RF shielding may also be actively or passively cooled.

In some embodiments, an MPI receiver system is included in the magnetic particle actuator system. This system may include a gradiometric receiver coil and low power receiver electronics configured to match the bandwidth of an anticipated MPI signal. For example, in some embodiments, the MPI receiver system may be sensitive to some number of the harmonics of the fundamental RF excitation frequency of the RF actuator system. In other embodiments, a greatly reduced bandwidth, such as a small bandwidth around the third harmonic of the fundamental frequency, may be supported.

In some embodiments, the MPI receiver system, in tandem with a control and reconstruction system, is capable of generating MPI images and reporting real-time MPI signals. In some embodiments, MPI images may be used as feedback to control actuation on a timescale consistent with MPI image acquisition and reconstruction. In other embodiments, real-time time-domain MPI signals are supported. In some embodiments, the real-time MPI signals from the MPI receiver system are provided to a control unit for presentation as real-time feedback to the user and/or used in a closed-loop feedback control of actuation. In some embodiments, MPI signals may be used alone or in combination with temperature sensors and other monitoring signals for real-time feedback and estimation of RF actuation dose. RF actuation dose estimations will depend on the application and may include SAR deposition, estimated temperature elevation, amount of drug released, actuation of a biomolecule, etc.

In a first mode of operation, a user first takes an image of the subject using an MPI system, a magnetic particle actuator system in imaging mode, or any other modality that is co-registerable with the magnetic particle actuator system (e.g., MRI, CT, X-Ray, optical, photograph, anatomic database, etc.). Co-registration (of images or of the modalities themselves) may be provided by, for example, fiducial markers distinct in both modalities, or an anatomical atlas. Target areas and any regions to avoid can be manually annotated by a user or automatically calculated from the co-registered modality. Therapeutic plan information may be entered for each target region by a user (e.g., Tx cassette to be used, duration of actuation, RF field strength, target energy deposition, target temperature, etc., and a therapeutic planning system will transform these inputs along with the ROI information into a specific therapeutic plan for each target region.

Figure 28:
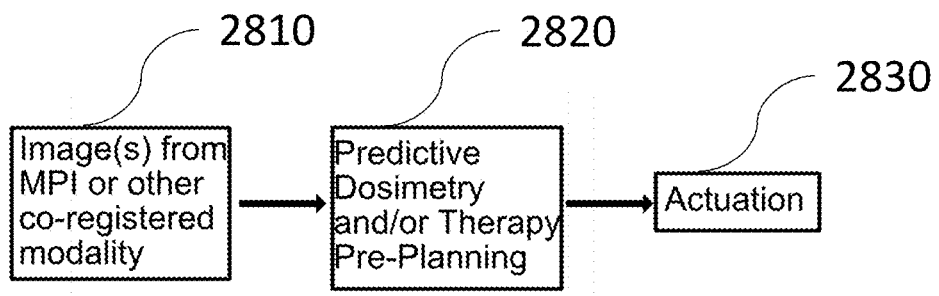
FIG. 28 is a diagram illustrating an exemplary open-loop workflow in accordance with certain aspects of the present disclosure.

To assist in therapeutic planning, energy deposition estimator tools may be used, taking advantage of information such as the known or anticipated concentration/dose of tracer at each target region (e.g., known from direct injection), and known MNP behavior. Furthermore, if the co-registered modality is an MPI system, image from the MPI system can be used in tandem or automatically to predict required dose/dose effects as an MPI image intensity is linearly proportional to the local MNP concentration. When the user is finished with inputting and a final therapeutic plan is produced, actuation can commence in an open-loop fashion as depicted in FIG. 28.

Accordingly, in some implementations, operations can further include obtaining, at 2810, an image of a patient, where the field-free region is located and/or shaped to approximately coincide with the target region identified based at least on the image. The image can be obtained from various modalities, including a magnetic particle imaging system, a magnetic resonance imaging system, an X-ray computed tomography system, an ultrasound system, or an optical fluorescent system. Then, at 2820, these images can be used for predictive dosimetry and/or therapy pre-planning. At 2830, matching of the FFR to target region(s) and/or actuation can commence.

Figure 29:
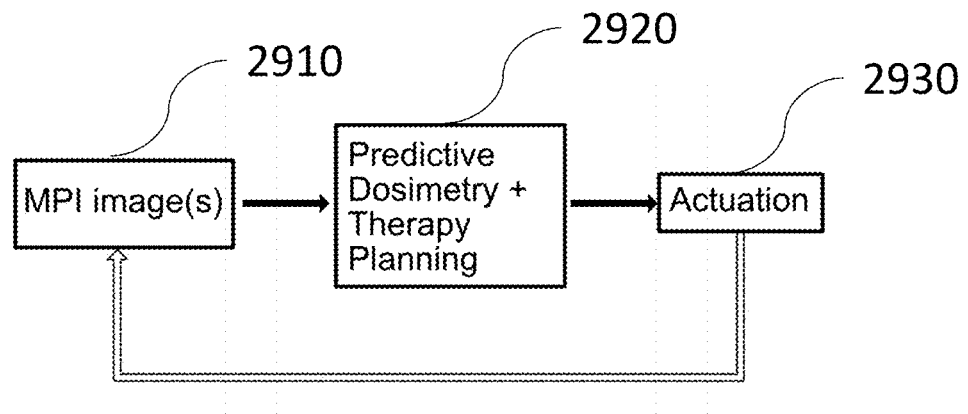
FIG. 29 is a diagram illustrating an exemplary closed loop workflow using images for actuation feedback in accordance with certain aspects of the present disclosure.

In a second mode of operation, any or all of the procedures of the first mode of operation may apply, but a feedback loop is introduced during actuation, as depicted in FIG. 29. In this implementation, the magnetic particle actuator system is capable of switching modes between RF actuation and MPI imaging. For example, MPI image acquisitions taking 1 second-60 minutes may be periodically interspersed with RF actuation steps and used to update actuation protocols. Updates may include taking into account changes in MNP distribution/concentration and any results of actuation detectable from the MPI signal. For example, MNPs may greatly change their MPI signal after significant heating (magnetic relaxation) or if heating/actuation disrupts an MNP carrier/delivery construct (e.g., agglomerates, drug carriers, etc.).

Accordingly, in some implementations, computer operations can further include generating or receiving a treatment plan for the target region, the treatment plan specifying the actuation to be delivered to the magnetic nanoparticles.

The closed loop portion of this second mode of operation is illustrated in FIG. 29. At 2910, one or more images of the patient can be received. At 2920, these images can be used to determine a modification to the actuation based on the information in the images, the treatment plan, and/or the output of a predicted dose based on the treatment plan and the images. For example, at 2930, the actuation can be automatically modified based at least on a change in the patient (e.g., patient motion, change in temperature, change in physiological characteristic such as heartbeat or respiration, etc.), based on a change in the magnetic nanoparticles as determined from the one or more images (e.g., magnetic nanoparticle distribution, release of carried drugs, etc.), or based on a change in a predicted dose (e.g., as received from a dose prediction program utilizing the images). The excitation field then can be applied to effect the modified actuation. Examples of modifying the actuation can include, for example, modifying a magnitude of the excitation field or modifying a period of time of applying the excitation field based at least on the change in the patient, magnetic nanoparticles, or the predicted dose.

Given the similar physics between the magnetic nanoparticle actuation methods described herein and magnetic particle imaging, in some implementations, the one or more images are generated by a magnetic particle imaging system that includes the magnet system and utilizes the field-free region. In other implementations, the images can be generated by a magnetic resonance imaging system or an X-ray computed tomography system and can be co-registered to the magnet system.

Figure 30:
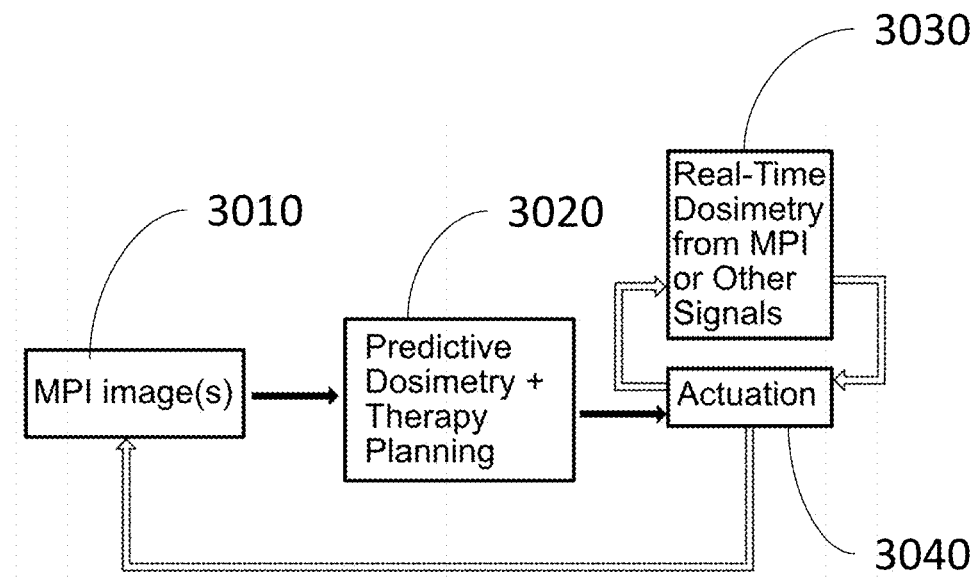
FIG. 30 is a diagram illustrating an exemplary closed loop workflow using real-time dosimetry for actuation feedback in accordance with certain aspects of the present disclosure.

In a third mode of operation, any or all of the procedures of the first two modes of operation may apply (though not necessarily without modification), but as depicted in FIG. 30, a second feedback loop incorporating rapid dosimetry can also be introduced during actuation. In this manner, fully simultaneous/parallel and real-time MPI (or other imaging modality) signal information can be incorporated. Because a common physics underlies MPI signal generation and RF actuation, a MPI signal will exist during actuation and may be used in tight actuation feedback loops. For example, one or more aspects of the raw MPI signal may be calibrated to provide real-time RF energy/SAR/RF actuation estimates. Corrective or stabilizing actions may be taken by a controller based on this real-time feedback.

Furthermore, as depicted in FIG. 30, other non-MPI based real-time signals, such as temperature from thermal probes, may be also be provided to the control system in real-time to further augment the closed-loop actuation. In some embodiments, the raw MPI signal can be transformed into continuous estimations of RF actuation dose. As used herein, use of the terms "real-time" and "simultaneous" contemplate that there may be some minor delay due to latency or processing overhead in the system.

The addition of real-time actuation feedback to the process of FIG. 29 is illustrated in FIG. 30. In some implementations, at 3010, a magnetic particle imaging signal can be received simultaneously with application of the excitation field. This is similar to the implementation discussed in reference to FIG. 29, however, the signals are generally acquired and processed at a faster rate (e.g., greater than 10 Hz, greater than 100 Hz, greater than 1 kHz, greater than 10 kHz, greater than 100 kHz, or greater than 1 MHz) and are not necessarily transformed into an actual image. At 3020, these signals can be used to determine a modification to the actuation based on the information in the images, the treatment plan, and/or the output of a predicted dose based on the treatment plan and the images. Then, at 3030, an actuation dose can be determined based at least on a calculation using the magnetic particle imaging signal. At 3040, the excitation field can be modified based at least on the actuation dose.

In the following, further features, characteristics, and exemplary technical solutions of the present disclosure will be described in terms of items that may be optionally claimed in any combination:

Item 1. A computer program product comprising a non-transitory, machine-readable medium storing instructions which, when executed by at least one programmable processor, cause operations comprising:
generating a magnetic field with a magnet system, the magnetic field including a field-free region at least partially matching a target region; and applying an excitation field with an excitation system to cause actuation of magnetic nanoparticles in an actuation region.

Item 2. A magnetic particle actuating system comprising:
a magnet system configured to generate a magnetic field that includes a field-free region;
an excitation system configured to generate an excitation field to cause actuation of magnetic nanoparticles in an actuation region; and
a control system configured to control the magnet system to create a field-free region at least partially matching a target region.

Item 3: The magnetic particle actuating system or computer program product of any one of the preceding items, wherein at least partially matching the field-free region to the target region comprises enclosing the target region within the field-free region.

Item 4: The magnetic particle actuating system or computer program product of any one of the preceding claims, wherein at least partially matching the field-free region to the target region comprises conforming the field-free region to the target region.

Item 5: The magnetic particle actuating system or computer program product of any one of the preceding items, wherein at least partially matching the field-free region to the target region comprises avoiding overlap with a region to avoid.

Item 6: The magnetic particle actuating system or computer program product of any one of the preceding items, the operations further comprising determining additional target region(s) during a process of covering an entire therapeutic region to be actuated during a treatment, while avoiding actuation of a region to avoid.

Item 7: The magnetic particle actuating system or computer program product of any one of the preceding items, wherein the additional target regions are actuated in series.

Item 8: The magnetic particle actuating system or computer program product of any one of the preceding items, wherein the additional target regions are actuated in a continuous manner.

Item 9: The magnetic particle actuating system or computer program product of any one of the preceding items, wherein the entire therapeutic region to be actuated is essentially an entire patient, other than the region to avoid.

Item 10: The magnetic particle actuating system or computer program product of any one of the preceding items, wherein at least partially matching the field-free region to the target region includes translating the field-free region to the target region.

Item 11: The magnetic particle actuating system or computer program product of any one of the preceding items, wherein at least partially matching the field-free region to the target region includes scaling the field-free region.

Item 12: The magnetic particle actuating system or computer program product of any one of the preceding items, wherein at least partially matching the field-free region to the target region includes changing a shape of the field-free region.

Item 13: The magnetic particle actuating system or computer program product of any one of the preceding items, wherein at least partially matching the field-free region to the target region includes rotating the field-free region.

Item 14: The magnetic particle actuating system or computer program product of any one of the preceding items, wherein the at least partially matching the field-free region to the target region includes causing mechanical movement of one or more magnets or magnetic materials in the magnet system to translate, scale, rotate, or change the shape of the field-free region.

Item 15: The magnetic particle actuating system or computer program product of any one of the preceding items, wherein the magnet system includes a first set of magnets on either side of the field-free region and the at least partially matching the field-free region to the target region includes independently controlling at least one of the first set of magnets to translate along a first axis.

Item 16: The magnetic particle actuating system or computer program product of any one of the preceding items, wherein the at least partially matching the field-free region to the target region includes causing mechanical translation of the first set of magnets along a second axis.

Item 17: The magnetic particle actuating system or computer program product of any one of the preceding items, wherein the magnet system includes a second set of magnets on either side of the field-free region and oriented along a second axis that is different than the first axis, wherein the at least partially matching further includes independently controlling at least one of the second set of magnets to translate along the second axis.

Item 18: The magnetic particle actuating system or computer program product of any one of the preceding items, wherein the magnet system includes a Halbach array that includes a plurality of magnetic materials and the at least partially matching the field-free region to the target region includes controlling one or more of the magnetic materials to move to a specified radial distance from a center of the Halbach array.

Item 19: The magnetic particle actuating system or computer program product of any one of the preceding items, wherein the plurality of magnetic materials in the Halbach array are disposed in a circular configuration having a diameter, and the at least partially matching the field-free region to the target region includes controlling the plurality of magnetic materials in the Halbach array to move radially to change the diameter of the Halbach array.

Item 20: The magnetic particle actuating system or computer program product of any one of the preceding items, wherein the magnet system includes one or more electromagnets and the at least partially matching the field-free region to the target region is based at least on controlling current(s) in the one or more electromagnets.

Item 21: The magnetic particle actuating system or computer program product of any one of the preceding items, wherein the at least partially matching the field-free region to the target region includes causing mechanical movement of one or more permanent magnets and causing mechanical movement of one or more magnetic materials that is not permanently magnetized, and controlling current(s) in one or more electromagnets to translate, scale, rotate, or change the shape of the field-free region.

Item 22: The magnetic particle actuating system or computer program product of any one of the preceding items, wherein the at least partially matching the field-free region to the target region includes controlling reorientation of a patient couch.

Item 23: The magnetic particle actuating system or computer program product of any one of the preceding items, the operations further comprising applying the excitation field through an excitation system.

Item 24: The magnetic particle actuating system or computer program product of any one of the preceding items, the operations further including generating the excitation field in a manner that changes the actuation region.

Item 25: The magnetic particle actuating system or computer program product of any one of the preceding items, wherein the generating of the excitation field is performed through a single RF coil.

Item 26: The magnetic particle actuating system or computer program product of any one of the preceding items, wherein the generating of the excitation field is performed through multiple independently controllable RF coils to enable changing the actuation region along multiple axes.

Item 27: The magnetic particle actuating system or computer program product of any one of the preceding items, wherein the generating of the excitation field is performed through a solenoidal RF coil and multiple saddle RF coils.

Item 28: The magnetic particle actuating system or computer program product of any one of the preceding items, wherein the multiple independently controllable RF coils allow selection of an RF vector along which the actuation region is changed through specifying currents through the multiple independently controllable RF coils.

Item 29: The magnetic particle actuating system or computer program product of any one of the preceding items, wherein the generating of the excitation field is performed through at least one spatially inhomogeneous RF coil.

Item 30: The magnetic particle actuating system or computer program product of any one of the preceding items, wherein avoiding actuation of the region to avoid includes causing placement of a passive component that shapes the excitation field.

Item 31: The magnetic particle actuating system or computer program product of any one of the preceding items, wherein the passive component includes one or more wire loops.

Item 32: The magnetic particle actuating system or computer program product of any one of the preceding items, wherein the excitation system includes a swappable cassette in which portions of the excitation system are included and which can be swapped out of the magnet system for different performance or different therapies.

Item 33: The magnetic particle actuating system or computer program product of any one of the preceding items, the operations further comprising obtaining an image of a patient, wherein the field-free region is located and/or shaped to approximately coincide with the target region identified based at least on the image.

Item 34: The magnetic particle actuating system or computer program product of any one of the preceding items, wherein the image is obtained from a magnetic particle imaging system.

Item 35: The magnetic particle actuating system or computer program product of any one of the preceding items, wherein the image is obtained from a magnetic resonance imaging system, an X-ray computed tomography system, an ultrasound system, or an optical fluorescence system.

Item 36: The magnetic particle actuating system or computer program product of any one of the preceding items, the operations further comprising:
receiving a treatment plan for the target region, the treatment plan specifying the actuation to be delivered to the magnetic nanoparticles;
generating or receiving one or more images of the patient;
automatically modifying the actuation based at least on a change in the patient, a change in the magnetic nanoparticles, or a change in a predicted dose as determined from the one or more images; and
applying the excitation field to perform the modified actuation.

Item 37: The magnetic particle actuating system or computer program product of any one of the preceding items, wherein modifying the actuation includes modifying a magnitude of the excitation field or modifying a period of time of applying the excitation field based at least on the change in the patient, the magnetic nanoparticles, or the predicted dose.

Item 38: The magnetic particle actuating system or computer program product of any one of the preceding items, wherein the one or more images are generated by a magnetic particle imaging system that includes the magnet system and utilizes the field-free region.

Item 39: The magnetic particle actuating system or computer program product of any one of the preceding items, wherein the one or more images are generated by a magnetic resonance imaging system or an X-ray computed tomography system, the operations further comprising co-registering the one or more images to the magnet system.

Item 40: The magnetic particle actuating system or computer program product of any one of the preceding items, the operations further comprising:
receiving a magnetic particle imaging signal simultaneously with application of the excitation field;
determining an actuation dose based at least on a calculation using the magnetic particle imaging signal; and
modifying the excitation field based at least on the actuation dose.

Item 41: The magnetic particle actuating system or computer program product of any one of the preceding items, wherein the control system is further configured to control the magnet system to cause the field-free region to enclose the target region.

Item 42: The magnetic particle actuating system or computer program product of any one of the preceding items, wherein the control system is further configured to control the magnet system to cause the field-free region to conform to the target region.

Item 43: The magnetic particle actuating system or computer program product of any one of the preceding items, wherein the control system is further configured to control the magnet system to cause the field-free region to avoid overlap with a region to avoid.

Item 44: The magnetic particle actuating system or computer program product of any one of the preceding items, wherein the control system is further configured to determine additional target region(s) for a process of covering an entire therapeutic region to be actuated during a treatment, while avoiding actuation of a region to avoid.

Item 45: The magnetic particle actuating system or computer program product of any one of the preceding items, wherein the control system is further configured to actuate the additional target regions in series.

Item 46: The magnetic particle actuating system or computer program product of any one of the preceding items, wherein the control system is further configured to actuate the additional target regions in a continuous manner.

Item 47: The magnetic particle actuating system or computer program product of any one of the preceding items, wherein the control system is further configured to actuate essentially an entire patient, other than the region to avoid.

Item 48: The magnetic particle actuating system or computer program product of any one of the preceding items, wherein the control system is further configured to control the magnet system to translate the field-free region to the target region as part of the at least partial matching of the field-free region to the target region.

Item 49: The magnetic particle actuating system or computer program product of any one of the preceding items, wherein the control system is further configured to control the magnet system to scale the field-free region to the target region as part of the at least partial matching of the field-free region to the target region.

Item 50: The magnetic particle actuating system or computer program product of any one of the preceding items, wherein the control system is further configured to control the magnet system to change a shape of the field-free region to the target region as part of the at least partial matching of the field-free region to the target region.

Item 51: The magnetic particle actuating system or computer program product of any one of the preceding items, wherein the control system is further configured to control the magnet system to rotate the field-free region to the target region as part of the at least partial matching of the field-free region to the target region.

Item 52: The magnetic particle actuating system or computer program product of any one of the preceding items, the magnet system further comprising:
one or more magnetic materials; and
wherein the control system is further configured to cause mechanical movement of the one or more magnetic materials to translate, scale, rotate, or change the shape of the field-free region.

Item 53: The magnetic particle actuating system or computer program product of any one of the preceding items, the magnet system further comprising:
a first set of magnets on either side of the field-free region; and
a first magnet stage system configured to independently translate at least one of the first set of magnets along a first axis; and
wherein the control system is further configured to control at least one of the first set of magnets to translate along the first axis as part of the at least partial matching of the field-free region to the target region.

Item 54: The magnetic particle actuating system or computer program product of any one of the preceding items, wherein the first magnet stage system is further configured to independently translate the at least one of the first set of magnets along a second axis; and
wherein the control system is further configured to cause mechanical translation of the first set of magnets along a second axis as part of the at least partial matching of the field-free region to the target region.

Item 55: The magnetic particle actuating system or computer program product of any one of the preceding items, the magnet system further comprising:
a second set of magnets on either side of the field-free region; and
a second magnet stage system configured to independently translate at least one of the second set of magnets along a second axis; and
wherein the control system is further configured to control at least one of the second set of magnets to translate along the second axis as part of the at least partial matching of the field-free region to the target region.

Item 56: The magnetic particle actuating system or computer program product of any one of the preceding items, the magnet system further comprising:
a Halbach array that includes a plurality of magnetic materials; and
wherein the control system is further configured to move one or more of the plurality of magnetic materials to a specified radial distance as part of the at least partial matching of the field-free region to the target region.

Item 57: The magnetic particle actuating system or computer program product of any one of the preceding items, wherein the plurality of magnetic materials in the Halbach array are disposed in a circular configuration having a diameter; and
wherein the control system is further configured to control the plurality of magnetic materials to move radially to change the diameter of the Halbach array as part of the at least partial matching of the field-free region to the target region.

Item 58: The magnetic particle actuating system or computer program product of any one of the preceding items, the magnet system further comprising one or more electromagnets; and
wherein the control system is further configured to control currents in the one or more electromagnets as part of the at least partial matching of the field-free region to the target region.

Item 59: The magnetic particle actuating system or computer program product of any one of the preceding items, the magnet system further comprising one or more permanent magnets, one or more magnetic materials that is not permanently magnetized, and one or more electromagnets; and
wherein the control system is further configured to cause mechanical movement of the one or more permanent magnets and cause mechanical movement of the one or more magnetic materials that is not permanently magnetized and control current(s) in the one or more electromagnets to translate, scale, rotate, or change the shape of the field-free region.

Item 60: The magnetic particle actuating system or computer program product of any one of the preceding items, further comprising:
a patient couch; and
wherein the control system is further configured to control reorientation of the patient couch as part of the at least partial matching of the field-free region to the target region.

Item 61: The magnetic particle actuating system or computer program product of any one of the preceding items, wherein the control system is further configured to cause the excitation system to generate the excitation field in a manner that changes the actuation region.

Item 62: The magnetic particle actuating system or computer program product of any one of the preceding items, wherein the excitation system includes a single RF coil; and
wherein the control system is further configured to cause the excitation system to generate the excitation field with the single RF coil.

Item 63: The magnetic particle actuating system or computer program product of any one of the preceding items, wherein the excitation system includes multiple independently controllable RF coils; and wherein the control system is further configured to cause the excitation system to generate the excitation field along multiple axes utilizing the multiple independently controllable RF coils.

Item 64: The magnetic particle actuating system or computer program product of any one of the preceding items, wherein the excitation system includes a solenoidal RF coil and multiple saddle RF coils; and
wherein the control system is further configured to cause the excitation system to generate the excitation field utilizing the solenoidal RF coil and the multiple saddle RF coils.

Item 65: The magnetic particle actuating system or computer program product of any one of the preceding items, wherein the control system is further configured to control the multiple independently controllable RF coils to allow selection of an RF vector along which the actuation region is changed through specifying currents through the multiple independently controllable RF coils.

Item 66: The magnetic particle actuating system or computer program product of any one of the preceding items, wherein the excitation system includes at least one spatially inhomogeneous RF coil; and
wherein the control system is further configured to cause the excitation system to generate the excitation field utilizing the at least one spatially inhomogeneous RF coil.

Item 67: The magnetic particle actuating system or computer program product of any one of the preceding items, further comprising a passive component; and
wherein the control system is further configured to cause placement of the passive component to shape the excitation field and avoid actuation of the region to avoid.

Item 68: The magnetic particle actuating system or computer program product of any one of the preceding items, wherein the passive component includes one or more wire loops.

Item 69: The magnetic particle actuating system or computer program product of any one of the preceding items, wherein the excitation system includes a swappable cassette containing at least a portion of the excitation system.

Item 70: The magnetic particle actuating system or computer program product of any one of the preceding items, further comprising an RF shield disposed between a portion of the excitation system and a portion of the magnet system to reduce interference of the excitation system during the generation of the excitation field.

Item 71: The magnetic particle actuating system or computer program product of any one of the preceding items, wherein the RF shield is a tube made of copper, steel, or aluminum.

Item 72: The magnetic particle actuating system or computer program product of any one of the preceding items, wherein the portion of the excitation system is inside the RF shield and includes one or more RF coils, and wherein the portion of the magnet system is outside the RF shield and includes one or more magnets of the magnet system.

Item 73: The magnetic particle actuating system or computer program product of any one of the preceding items, further comprising one or more RF receiver coils, wherein the RF shield is disposed between the one or more RF receiver coils and the portion of the magnet system.

Item 74: The magnetic particle actuating system or computer program product of any one of the preceding items, wherein the control system is further configured to:
receive a treatment plan for the target region, the treatment plan specifying the actuation to be delivered to the magnetic nanoparticles; and
generate or receive one or more images of the patient;
automatically modify the actuation based at least on a change in the patient, a change in the magnetic nanoparticles, or a change in a predicted dose as determined from the one or more images; and
apply the excitation field to perform the modified actuation.

Item 75: The magnetic particle actuating system or computer program product of any one of the preceding items, wherein the modifying of the actuation is performed by the control system that is further configured to modify a magnitude of the excitation field or modify a period of time of applying the excitation field based at least on the change in the patient, the magnetic nanoparticles, or the predicted dose.

Item 76: The magnetic particle actuating system or computer program product of any one of the preceding items, wherein the magnetic particle imaging system that includes the magnet system and utilizes the field-free region is configured to generate the one or more images.

Item 77: The magnetic particle actuating system or computer program product of any one of the preceding items, wherein the one or more images are received from a magnetic resonance imaging system or an X-ray computed tomography system, and
wherein the control system is further configured to co-register the one or more images to the magnet system.

Item 78: The magnetic particle actuating system or computer program product of any one of the preceding items, the wherein the control system is further configured to:
receive a magnetic particle imaging signal simultaneously with application of the excitation field;
determine an actuation dose based at least on a calculation using the magnetic particle imaging signal; and
modify the excitation field based at least on the actuation dose.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A computer program product comprising a non-transitory, machine-readable medium storing instructions which, when executed by at least one programmable processor, cause operations comprising:
    generating a magnetic field with a magnet system, the magnetic field including a field-free region enclosing a target region within the field-free region, the generating of the magnetic field utilizing coils with currents flowing in opposite directions to generate opposing magnetic fields; and
    applying an excitation field with an excitation system to cause actuation of magnetic nanoparticles in an actuation region.

2. The computer program product of claim 1, the operations further comprising determining additional target region(s) during a process of covering an entire therapeutic region to be actuated during a treatment, while avoiding actuation of a region to avoid, wherein the additional target regions are actuated in a continuous manner.

3. The computer program product of claim 1, the operations further comprising determining additional target region(s) during a process of covering an entire therapeutic region to be actuated during a treatment, while avoiding actuation of a region to avoid, wherein the entire therapeutic region to be actuated is essentially an entire patient, other than the region to avoid.

4. The computer program product of claim 1, wherein the magnet system includes a first set of magnets on either side of the field-free region and the enclosing of the target region within the field-free region includes independently controlling at least one of the first set of magnets to translate along a first axis,
wherein the magnet system includes a second set of magnets on either side of the field-free region and oriented along a second axis that is different than the first axis, wherein the enclosing further includes independently controlling at least one of the second set of magnets to translate along the second axis.

5. The computer program product of claim 1, wherein the magnet system includes a Halbach array that includes a plurality of magnetic materials and the enclosing of the target region within the field-free region includes controlling one or more of the magnetic materials to move to a specified radial distance from a center of the Halbach array.

6. The computer program product of claim 5, wherein the plurality of magnetic materials in the Halbach array are disposed in a circular configuration having a diameter, and the enclosing of the target region within the field-free region includes controlling the plurality of magnetic materials in the Halbach array to move radially to change the diameter of the Halbach array.

7. The computer program product of claim 1, wherein the enclosing of the target region within the field-free region includes causing mechanical movement of one or more permanent magnets and causing mechanical movement of one or more magnetic materials that is not permanently magnetized, and controlling current(s) in one or more electromagnets to translate, scale, rotate, or change the shape of the field-free region.

8. The computer program product of claim 1, wherein generating of the excitation field is performed through multiple independently controllable radio frequency (RF) coils to enable changing the actuation region along multiple axes.

9. The computer program product of claim 8, wherein the generating of the excitation field is performed through the multiple independently controllable RF coils that include a solenoidal RF coil and multiple saddle RF coils.

10. The computer program product of claim 1, wherein generating of the excitation field is performed through at least one spatially inhomogeneous RF coil.

11. A magnetic particle actuating system comprising:
a magnet system configured to generate a magnetic field that includes a field-free region;
an excitation system configured to generate an excitation field to cause actuation of magnetic nanoparticles in an actuation region, the generating of the magnetic field utilizing coils with currents flowing in opposite directions to generate opposing magnetic fields; and
a control system configured to control the magnet system to cause the field-free region to enclose a target region within the field-free region.

12. The magnetic particle actuating system of claim 11, wherein the control system is further configured to determine additional target region(s) for a process of covering an entire therapeutic region to be actuated during a treatment, while avoiding actuation of a region to avoid.

13. The magnetic particle actuating system of claim 11, the magnet system further comprising:
a first set of magnets on either side of the field-free region; and
a first magnet stage system configured to independently translate at least one of the first set of magnets along a first axis; and
wherein the control system is further configured to control at least one of the first set of magnets to translate along the first axis as part of the enclosing of the field-free region to the target region.

14. The magnetic particle actuating system of claim 11, the magnet system further comprising:
a Halbach array that includes a plurality of magnetic materials; and
wherein the control system is further configured to move one or more of the plurality of magnetic materials to a specified radial distance from a center of the Halbach array as part of the enclosing of the field-free region to the target region.

15. The magnetic particle actuating system of claim 14, wherein the plurality of magnetic materials in the Halbach array are disposed in a circular configuration having a diameter; and
wherein the control system is further configured to control the plurality of magnetic materials to move radially to change the diameter of the Halbach array as part of the enclosing of the field-free region to the target region.

16. The magnetic particle actuating system of claim 11, the magnet system further comprising one or more permanent magnets, one or more magnetic materials that is not permanently magnetized, and one or more electromagnets; and
wherein the control system is further configured to cause mechanical movement of the one or more permanent magnets and cause mechanical movement of the one or more magnetic materials that is not permanently magnetized and control current(s) in the one or more electromagnets to translate, scale, rotate, or change the shape of the field-free region.

17. The magnetic particle actuating system of claim 11, wherein the control system is further configured to cause the excitation system to generate the excitation field in a manner that changes the actuation region,
wherein the excitation system includes multiple independently controllable radio frequency (RF) coils that include a solenoidal RF coil and multiple saddle RF coils,
wherein the control system is further configured to cause the excitation system to generate the excitation field along multiple axes utilizing the multiple independently controllable RF coils, and
wherein the control system is further configured to cause the excitation system to generate the excitation field utilizing the solenoidal RF coil and the multiple saddle RF coils.

18. The magnetic particle actuating system of claim 11, wherein the control system is further configured to cause the excitation system to generate the excitation field in a manner that changes the actuation region,
wherein the excitation system includes at least one spatially inhomogeneous RF coil, and
wherein the control system is further configured to cause the excitation system to generate the excitation field utilizing the at least one spatially inhomogeneous RF coil.

19. The magnetic particle actuating system of claim 11, wherein the control system is further configured to determine additional target region(s) for a process of covering an entire therapeutic region to be actuated during a treatment, while avoiding actuation of a region to avoid, further comprising a passive component; and wherein the control system is further configured to cause placement of the passive component to shape the excitation field and avoid actuation of the region to avoid.

* * * * *